(12) United States Patent
Hayden et al.

(10) Patent No.: US 11,793,685 B2
(45) Date of Patent: Oct. 24, 2023

(54) ABSORBENT ARTICLE HAVING FASTENING SYSTEM

(71) Applicant: The Procter & Gamble Company, Cincinnati, OH (US)

(72) Inventors: Russell Andrew Hayden, New Richmond, OH (US); Abhishek Prakash Surushe, Schwalbach am Taunus (DE); Jeromy Thomas Raycheck, South Lebanon, OH (US); Kumardipti Chatterjee, Indian Hill, OH (US); Donald Carroll Roe, West Chester, OH (US); Alejandro Jose Rivero, São Paulo (BR)

(73) Assignee: The Procter and Gamble Company, Cincinnati, OH (US)

( * ) Notice: Subject to any disclaimer, the term of this patent is extended or adjusted under 35 U.S.C. 154(b) by 591 days.

(21) Appl. No.: 16/685,230

(22) Filed: Nov. 15, 2019

(65) Prior Publication Data

US 2021/0145661 A1    May 20, 2021

(51) Int. Cl.
*A61F 13/56* (2006.01)
*A61F 13/49* (2006.01)

(52) U.S. Cl.
CPC .... *A61F 13/5644* (2013.01); *A61F 13/49011* (2013.01)

(58) Field of Classification Search
CPC ...... A61F 13/5644; A61F 13/00; A61F 13/49; A61F 13/49011; A61F 13/49012;
(Continued)

(56) References Cited

U.S. PATENT DOCUMENTS

| D132,937 S | 6/1942 | Cadgene |
|---|---|---|
| 3,658,064 A | 4/1972 | Pociluyko |

(Continued)

FOREIGN PATENT DOCUMENTS

| CN | 101346118 A | 1/2009 |
|---|---|---|
| CN | 102427786 A | 4/2012 |

(Continued)

OTHER PUBLICATIONS

International Search Report and Written Opinion; Application Ser. No. PCT/US2020/070766; dated Mar. 12, 2021, 13 pages.
(Continued)

*Primary Examiner* — Susan S Su
(74) *Attorney, Agent, or Firm* — Sarah M. DeCristofaro; Wednesday Shipp

(57) ABSTRACT

An absorbent article has a first waist region, a second waist region, a crotch region disposed between the first and second waist regions; and a chassis comprising a topsheet, a backsheet, and an absorbent core disposed between the topsheet and backsheet. The article also includes a primary fastening system and secondary fastening system. The primary fastening system has a primary fastening component disposed in the second waist region and a primary receiving component disposed in the first waist region and operatively engageable with the primary fastening component. The secondary fastening system includes a secondary fastening component disposed in the first waist region and a secondary receiving component disposed in the second waist region and operatively engageable with the secondary fastening component. The article further includes a decoupled zone disposed longitudinally inboard of the secondary fastening component.

18 Claims, 18 Drawing Sheets

(58) Field of Classification Search
CPC ......... A61F 13/49014; A61F 13/49015; A61F 13/49061
USPC .................................................. 604/358–392
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,610,678 A | 9/1986 | Weisman et al. | |
| 4,662,875 A | 5/1987 | Hirotsu | |
| 4,673,402 A | 6/1987 | Weisman | |
| 4,699,622 A | 10/1987 | Toussant | |
| 4,808,178 A | 2/1989 | Aziz | |
| 4,834,735 A | 5/1989 | Alemany | |
| 4,834,741 A | 5/1989 | Sabee | |
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,909,803 A | 3/1990 | Aziz | |
| 4,946,527 A | 8/1990 | Battrell | |
| 4,963,140 A | 10/1990 | Robertson | |
| 4,990,147 A | 2/1991 | Freeland | |
| 5,037,416 A | 8/1991 | Allen et al. | |
| 5,137,537 A | 8/1992 | Herron | |
| 5,147,345 A | 9/1992 | Lavon | |
| 5,151,092 A | 9/1992 | Buell | |
| 5,156,793 A | 10/1992 | Buell et al. | |
| 5,167,897 A | 12/1992 | Weber et al. | |
| 5,221,274 A | 6/1993 | Buell | |
| 5,242,436 A * | 9/1993 | Weil .................. | A61F 13/58 604/386 |
| 5,260,345 A | 11/1993 | Desmarais | |
| 5,269,775 A | 12/1993 | Freeland et al. | |
| 5,342,338 A | 8/1994 | Roe | |
| 5,387,207 A | 2/1995 | Dyer | |
| 5,397,316 A | 3/1995 | Young | |
| 5,499,978 A | 3/1996 | Buell | |
| 5,507,736 A | 4/1996 | Clear | |
| 5,554,145 A | 9/1996 | Roe | |
| 5,569,234 A | 10/1996 | Buell | |
| 5,571,096 A | 11/1996 | Dobrin | |
| 5,580,411 A | 12/1996 | Nease | |
| 5,591,152 A | 1/1997 | Buell | |
| D377,979 S | 2/1997 | Swenson et al. | |
| 5,607,760 A | 3/1997 | Roe | |
| 5,609,587 A | 3/1997 | Roe | |
| 5,625,222 A | 4/1997 | Yoneda | |
| 5,635,191 A | 6/1997 | Roe et al. | |
| 5,643,588 A | 7/1997 | Roe et al. | |
| D384,152 S | 9/1997 | Raufman | |
| D403,400 S | 12/1998 | Dreier et al. | |
| D403,401 S | 12/1998 | Dreier et al. | |
| D403,402 S | 12/1998 | Dreier et al. | |
| 5,851,205 A | 12/1998 | Hisada et al. | |
| 5,865,823 A | 2/1999 | Curro | |
| 5,993,432 A | 11/1999 | Lodge et al. | |
| 6,004,306 A | 12/1999 | Robles | |
| D428,142 S | 7/2000 | Stromblad | |
| 6,107,537 A | 8/2000 | Elder et al. | |
| 6,120,487 A | 9/2000 | Ashton | |
| 6,132,410 A | 10/2000 | Gompel et al. | |
| D435,103 S | 12/2000 | Schmoker | |
| 6,195,850 B1 | 3/2001 | Melbye et al. | |
| 6,248,097 B1 | 6/2001 | Beitz et al. | |
| D448,079 S | 9/2001 | Bruemmer-prestley | |
| 6,336,922 B1 | 1/2002 | Vangompel et al. | |
| 6,410,129 B2 | 6/2002 | Zhang et al. | |
| 6,432,098 B1 | 8/2002 | Kline et al. | |
| 6,478,784 B1 * | 11/2002 | Johnson ................ | A61F 13/625 24/442 |
| 6,677,258 B2 | 1/2004 | Carroll et al. | |
| 6,746,434 B2 | 6/2004 | Johnson | |
| 6,843,134 B2 | 1/2005 | Anderson et al. | |
| 6,945,968 B2 | 9/2005 | Svensson et al. | |
| 7,062,983 B2 | 6/2006 | Anderson et al. | |
| D543,276 S | 5/2007 | Martynus et al. | |
| D544,098 S | 6/2007 | Martynus et al. | |
| 7,435,243 B2 | 10/2008 | Miyamoto | |
| D581,525 S | 11/2008 | Zink, II et al. | |
| D583,469 S | 12/2008 | Zink, II et al. | |
| 7,626,073 B2 | 12/2009 | Catalan | |
| 7,744,576 B2 | 6/2010 | Busam | |
| 7,750,203 B2 | 7/2010 | Becker et al. | |
| 7,806,883 B2 | 10/2010 | Fossum et al. | |
| 7,819,853 B2 | 10/2010 | Desai et al. | |
| 7,867,213 B2 | 1/2011 | Bandorf et al. | |
| 8,062,279 B2 | 11/2011 | Miyamoto | |
| 8,145,338 B2 | 3/2012 | Kent et al. | |
| 8,145,343 B2 | 3/2012 | Debruler | |
| 8,145,344 B2 | 3/2012 | Debruler | |
| 8,227,071 B2 | 7/2012 | Wood et al. | |
| 8,244,393 B2 | 8/2012 | Mclaughlin | |
| 8,454,571 B2 | 6/2013 | Rezai | |
| 8,618,350 B2 | 12/2013 | Mansfield | |
| 8,663,186 B2 | 3/2014 | Lam et al. | |
| 8,712,573 B2 | 4/2014 | Debruler et al. | |
| 8,712,574 B2 | 4/2014 | Debruler et al. | |
| 8,784,722 B2 | 7/2014 | Rocha | |
| 8,795,809 B2 | 8/2014 | Mansfield | |
| 8,939,957 B2 | 1/2015 | Raycheck et al. | |
| 8,992,500 B2 | 3/2015 | Fujioka | |
| 9,119,751 B2 | 9/2015 | Waksmundzki et al. | |
| 9,138,362 B2 | 9/2015 | Popp | |
| 9,265,673 B2 | 2/2016 | Stabelfeldt | |
| 9,265,674 B2 | 2/2016 | Hancock-cooke | |
| 9,301,889 B2 | 4/2016 | Miyamoto | |
| 9,429,929 B2 | 8/2016 | Debruler et al. | |
| 9,468,265 B2 | 10/2016 | Horn et al. | |
| 9,468,569 B2 | 10/2016 | Hancock-cooke | |
| 9,610,202 B2 | 4/2017 | Rezai et al. | |
| 9,615,980 B2 | 4/2017 | Enz | |
| 9,867,743 B2 | 1/2018 | Stabelfeldt | |
| 9,962,296 B2 | 5/2018 | Mansfield | |
| 9,980,859 B2 | 5/2018 | Popp | |
| 10,034,802 B2 | 7/2018 | Macura et al. | |
| D825,055 S | 8/2018 | Hirsch | |
| 10,076,162 B2 | 9/2018 | Rocha | |
| 10,085,897 B2 | 10/2018 | Landgrebe et al. | |
| D879,972 S | 3/2020 | Caneppele et al. | |
| D889,640 S | 7/2020 | Raycheck et al. | |
| 10,798,997 B2 | 10/2020 | Rocha | |
| 11,026,851 B2 | 6/2021 | Saito et al. | |
| D928,310 S | 8/2021 | Chase et al. | |
| D936,845 S | 11/2021 | Hahn et al. | |
| 11,389,344 B2 | 7/2022 | Suyama | |
| 11,399,990 B2 | 8/2022 | Suyama | |
| 2002/0038110 A1 | 3/2002 | Kusibojoska et al. | |
| 2002/0058923 A1 | 5/2002 | Suprise et al. | |
| 2002/0193776 A1 | 12/2002 | Fernfors | |
| 2003/0009144 A1 | 1/2003 | Tanzer et al. | |
| 2003/0050616 A1 | 3/2003 | Reynolds et al. | |
| 2003/0135192 A1 * | 7/2003 | Guralski ........... | A61F 13/15747 604/391 |
| 2004/0082933 A1 | 4/2004 | Karami | |
| 2004/0181200 A1 | 9/2004 | Desai et al. | |
| 2004/0193133 A1 | 9/2004 | Desai et al. | |
| 2005/0079321 A1 | 4/2005 | Tuman et al. | |
| 2005/0222552 A1 | 10/2005 | Otsubo | |
| 2006/0129119 A1 | 6/2006 | Kistler | |
| 2006/0178651 A1 | 8/2006 | Glaug | |
| 2006/0212013 A1 | 9/2006 | Cohen et al. | |
| 2006/0287637 A1 | 12/2006 | Lam | |
| 2007/0073260 A1 | 3/2007 | Roe | |
| 2007/0219521 A1 | 9/2007 | Hird et al. | |
| 2007/0249254 A1 | 10/2007 | Mansfield | |
| 2007/0287983 A1 * | 12/2007 | Lodge ................ | A61F 13/5148 604/392 |
| 2007/0293111 A1 | 12/2007 | Mansfield | |
| 2009/0258210 A1 | 10/2009 | Iyad et al. | |
| 2009/0299323 A1 * | 12/2009 | Schlinz ................ | A61F 13/565 604/391 |
| 2010/0180407 A1 | 7/2010 | Rocha | |

(56) References Cited

U.S. PATENT DOCUMENTS

| | | |
|---|---|---|
| 2011/0092947 A1 | 4/2011 | Kline et al. |
| 2011/0106043 A1 | 5/2011 | Waksmundzki et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0152812 A1 | 6/2011 | Hird et al. |
| 2011/0155304 A1 | 6/2011 | Sakaguchi |
| 2011/0178486 A1 | 7/2011 | Beck et al. |
| 2011/0184372 A1 | 7/2011 | Esping |
| 2011/0208144 A1 | 8/2011 | Roe et al. |
| 2011/0319849 A1 | 12/2011 | Collias et al. |
| 2012/0095429 A1* | 4/2012 | Kobayashi ........ A61F 13/49011 604/385.16 |
| 2012/0316526 A1 | 12/2012 | Rosati et al. |
| 2013/0082418 A1 | 4/2013 | Curro et al. |
| 2013/0131625 A1 | 5/2013 | Schlinz |
| 2013/0226121 A1 | 8/2013 | Kikkawa et al. |
| 2013/0345657 A1* | 12/2013 | Nelson ............... A61F 13/49058 604/386 |
| 2014/0000003 A1 | 1/2014 | Ashraf et al. |
| 2014/0000070 A1 | 1/2014 | Ashraf et al. |
| 2014/0000784 A1 | 1/2014 | Rane et al. |
| 2014/0257227 A1* | 9/2014 | Roe ................... A61F 13/15268 604/385.14 |
| 2015/0032075 A1 | 1/2015 | Coenen et al. |
| 2015/0032079 A1 | 1/2015 | Enz et al. |
| 2015/0045758 A1 | 2/2015 | Goodlander et al. |
| 2015/0126955 A1 | 5/2015 | Sauer et al. |
| 2015/0173963 A1 | 6/2015 | Coe et al. |
| 2016/0250085 A1 | 9/2016 | Lavon et al. |
| 2016/0270977 A1 | 9/2016 | Surushe |
| 2016/0278994 A1 | 9/2016 | Martynus et al. |
| 2017/0056253 A1 | 3/2017 | Chester et al. |
| 2017/0056256 A1 | 3/2017 | Smith et al. |
| 2017/0326006 A1 | 11/2017 | Neubauer et al. |
| 2018/0042777 A1 | 2/2018 | Dalal et al. |
| 2018/0042778 A1 | 2/2018 | Lenser et al. |
| 2018/0243147 A1 | 8/2018 | Swedberg et al. |
| 2018/0271716 A1 | 9/2018 | Dalal |
| 2018/0271717 A1 | 9/2018 | Dria |
| 2018/0325753 A1 | 11/2018 | Vohwinkel |
| 2019/0060135 A1 | 2/2019 | Kawka |
| 2020/0054505 A1 | 2/2020 | Su et al. |
| 2020/0113749 A1 | 4/2020 | Surushe et al. |
| 2020/0179184 A1 | 6/2020 | Kaiser |
| 2021/0145650 A1 | 5/2021 | Surushe et al. |
| 2021/0145660 A1 | 5/2021 | Surushe et al. |
| 2021/0251824 A1 | 8/2021 | Roe |
| 2021/0386602 A1 | 12/2021 | Raycheck et al. |
| 2022/0257432 A1 | 8/2022 | Raycheck et al. |

FOREIGN PATENT DOCUMENTS

| | | | |
|---|---|---|---|
| CN | 103260569 | A | 8/2013 |
| CN | 104302261 | A | 1/2015 |
| CN | 105431122 | A | 3/2016 |
| CN | 105919731 | A | 9/2016 |
| CN | 206910449 | U | 1/2018 |
| EP | 1377214 | B1 | 4/2005 |
| EP | 2259763 | B1 | 6/2014 |
| JP | H11155906 | A | 6/1999 |
| JP | 2004508138 | A | 3/2004 |
| JP | 2006246999 | A | 9/2006 |
| JP | 2007521036 | A | 8/2007 |
| JP | 2009056001 | A | 3/2009 |
| WO | 9108725 | A1 | 6/1991 |
| WO | WO9516746 | | 6/1995 |
| WO | 0015069 | A1 | 3/2000 |
| WO | WO-0156526 A1 * | 8/2001 | ........... A61F 13/515 |
| WO | 2005016211 | A1 | 2/2005 |
| WO | 2005110731 | A2 | 11/2005 |
| WO | 2011129097 | A1 | 10/2011 |
| WO | 2015015334 | A1 | 2/2015 |
| WO | WO2016022629 | A1 | 2/2016 |
| WO | WO2019018721 | A1 | 1/2019 |
| WO | 2019145647 | A1 | 8/2019 |
| WO | 2020041271 | A1 | 2/2020 |

OTHER PUBLICATIONS

International Search Report and Written Opinion; Application Ser. No. PCT/US2020/070767; dated Mar. 5, 2021, 15 pages.

International Search Report and Written Opinion; Application Ser. No. PCT/US2020/070768; dated Mar. 11, 2021, 15 pages.

Unpublished U.S. Appl. No. 16/711,481, filed Dec. 12, 2019, to Russell Andrew Hayden et al.

Unpublished U.S. Appl. No. 16/711,485, filed Dec. 12, 2019, to Russell Andrew Hayden et al.

Ail Office Actions; U.S. Appl. No. 16/684,895.

Final Office Action; U.S. Appl. No. 16/711,481 dated Apr. 25, 2023, 10 pages.

Non-Final Office Action: U.S. Appl. No. 16/684,860, dated Aug. 3, 2023, 15 pages.

Non-Final Office Action; U.S. Appl. No. 16/711,481 dated Feb. 1, 2023, 09 pages.

Non-Final Office Action; U.S. Appl. No. 16/711,481 dated Jul. 28, 2022, 30 pages.

Non-Final Office Action; U.S. Appl. No. 16/711,485 dated Jul. 28, 2023, 30 pages.

Non-Final Office Action; U.S. Appl. No. 16/711,485 dated Feb. 3, 2023, 14 pages.

* cited by examiner

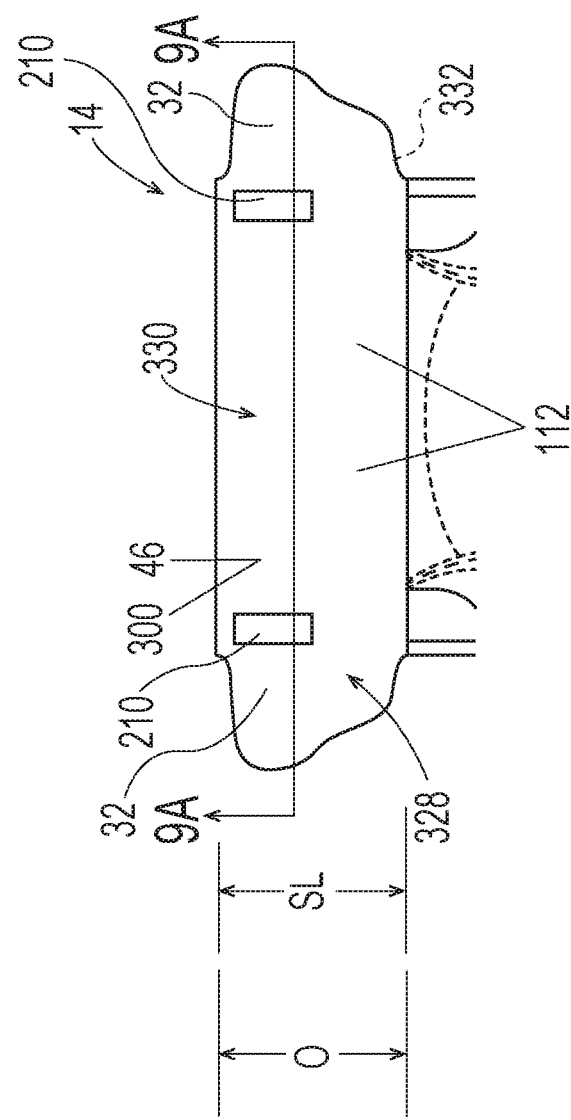

ABSORBENT ARTICLE HAVING FASTENING SYSTEM

FIELD OF THE INVENTION

The present disclosure relates to absorbent articles having fastening systems, in particular articles having multiple fastening systems.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer. Fastening systems have been used to ensure the article is secured about the wearer and remains in place. One popular configuration of absorbent article/fastening system includes an absorbent chassis having a front waist region, crotch region and rear waist region, with a pair of fastening members each extending respectively laterally from left and right longitudinal edges of the chassis in the rear waist region. In a typical configuration, each fastening member includes a patch of material bearing hooks, affixed to the wearer-facing side of the fastening member. A section of cooperating loops material is typically disposed on the garment-facing side of the front waist region. In this configuration, the chassis may be wrapped through the wearer's crotch area with the back waist region placed across the wearer's lower back and buttocks and the front waist region placed across the wearer's lower belly area. The left and right fastening members may then be wrapped about the wearer's left and right hips, respectively, and fastened to the front waist region via engagement of the hooks with the loops material on the front waist region, thereby securing the diaper on the wearer.

To further ensure fit and prolonged attachment about the waist, a secondary fastening system may be included, which may include hooks affixed to the garment-facing side of the front waist region and cooperating hook receiving material (e.g., loops) on the wearer-facing side of the back waist region. Because the secondary fastening system provides additional areas of attachment and anchoring, the front and back waist regions may better conform to the wearer, reducing gaps and sagging both at application and during use. The secondary fastening system also reduces potential rotation of the waist regions and/or flipping of material at the waist that often occurs when exudates weigh down the crotch region of the article.

While dual fastening systems provide better prolonged fit, the systems may cause skin irritation. In known dual fastening systems, a secondary fastener becomes the widest connection point between the front and back of the article. Once the article is loaded with fluid, a tension line forms between the fluid load, located proximate to the wearer's crotch, and the secondary fastener, located proximate to the wearer's hip. Material outboard of the tension line collapses, folds or otherwise deforms as the article narrows to fit the wearer's body, allowing the secondary fastening components (e.g., hooks) to contact the wearer's skin. The wearer may suffer skin abrasion from the surface of the component and/or may be poked by one or more corners of the component.

Therefore, there is a need for a better design for dual fastening systems that reduces skin irritation. There is a further need for dual fastening systems that maintain desired fit during wear and after loading. There is also a need to provide desired fastening properties in a cost efficient and effective manner.

SUMMARY OF THE INVENTION

An absorbent article comprises a first waist region, a second waist region, a crotch region disposed between the first and second waist regions; and a chassis having a topsheet, a backsheet, and an absorbent core disposed between the topsheet and backsheet. The article may further include a primary fastening system and secondary fastening system, wherein the primary fastening system comprises a primary fastening component disposed in the second waist region and a primary receiving component disposed in the first waist region and operatively engageable with the primary fastening component. The secondary fastening system comprises a secondary fastening component disposed in the first waist region and a secondary receiving component disposed in the second waist region and operatively engageable with the secondary fastening component.

The article may further comprise a composite having a lateral extension element and the chassis. The layers of the composite are joined in an anchoring zone, which is defined by a perimeter. A decoupled zone is adjacent to the anchoring zone and disposed outside of the perimeter. At least a portion of the secondary fastening component may be disposed in the anchoring zone, and a portion of the composite may be longitudinally inboard of the secondary fastening component and within the decoupled zone.

In some embodiments, the secondary fastening component may be at least partially disposed in a bending resistant zone of the first waist region. The bending resistant zone may comprise a stiffness of at least 0.2 N/mm.

In further embodiments, the anchoring zone may comprise a varied width having a maximum width, $W_{AZmax}$, and a minimum width, $W_{AZmin}$, wherein the maximum width, $W_{AZmax}$, is in an area that is longitudinally outboard of the minimum width.

BRIEF DESCRIPTION OF THE DRAWINGS

FIGS. 5A-5D are schematic plan views of nonlimiting embodiments of a waist region in FIG. 4 with layer(s) removed to reveal nonlimiting examples of areas of attachment.

FIG. 9 is a schematic plan view of an exemplary waist region according to a nonlimiting embodiment.

DETAILED DESCRIPTION OF THE INVENTION

Definitions

Figure 1:
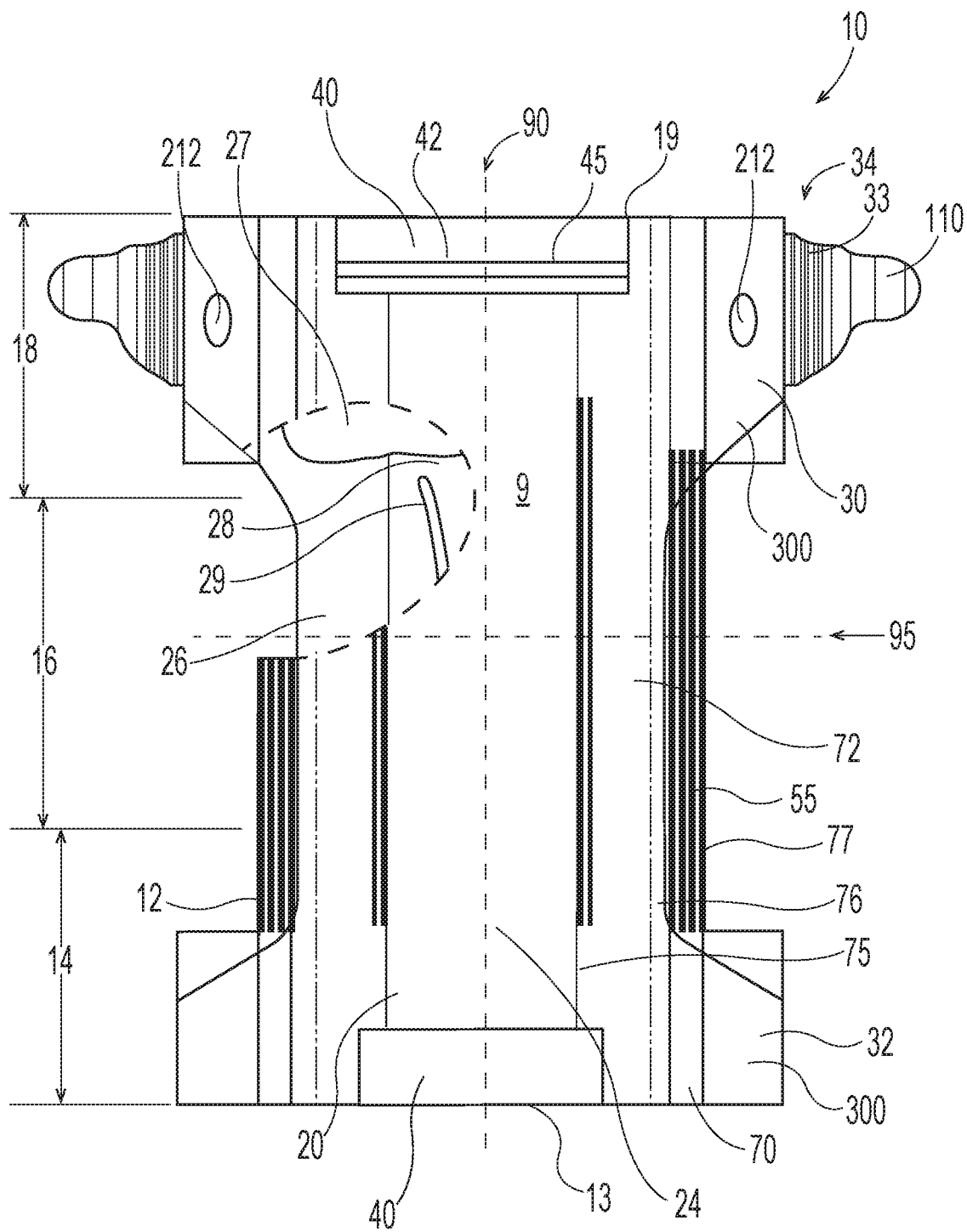
FIG. 1 is a schematic plan view of an exemplary absorbent article according to one nonlimiting embodiment of the present invention. The absorbent article is shown in a flat, uncontracted state.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Disposable," in reference to articles, means that the articles are generally not intended to be laundered or otherwise restored or reused in the same capacity (i.e., they are intended to be discarded after a single use and, preferably, to be recycled, composted or otherwise discarded in an environmentally compatible manner).

"Disposed" refers to an element being located in a particular place or position. A feature that is disposed on a surface or side of a component may be integral with said component or may be joined to said component.

"Elastic" and "elastomeric" mean the ability of a material to stretch by at least 100% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic.

"Extensible" means the ability to stretch or elongate, without rupture or breakage, by at least 50% as per step 5(a) in the Hysteresis Test herein (replacing the specified 100% strain with 50% strain).

"Inboard," with respect to a first feature of an article and its position relative a second feature or location on the article, means that the first feature lies closer to a respective axis of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal axis, and longitudinally inboard means the first feature is closer to the lateral axis. Conversely, "outboard," with respect to a first feature of an article and its position relative a second feature or location on the article, means that the first feature lies farther from the respective axis of the article than the second feature or location.

"Integral with" a component means being formed from or formed by said component, or portions thereof, as opposed to being joined to the component.

"Joined" means configurations whereby an element is directly secured to another element by affixing the element directly to the other element, and configurations whereby an element is indirectly secured to another element by affixing the element to intermediate member(s) that in turn are affixed to the other element.

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

Overview

Figure 2:
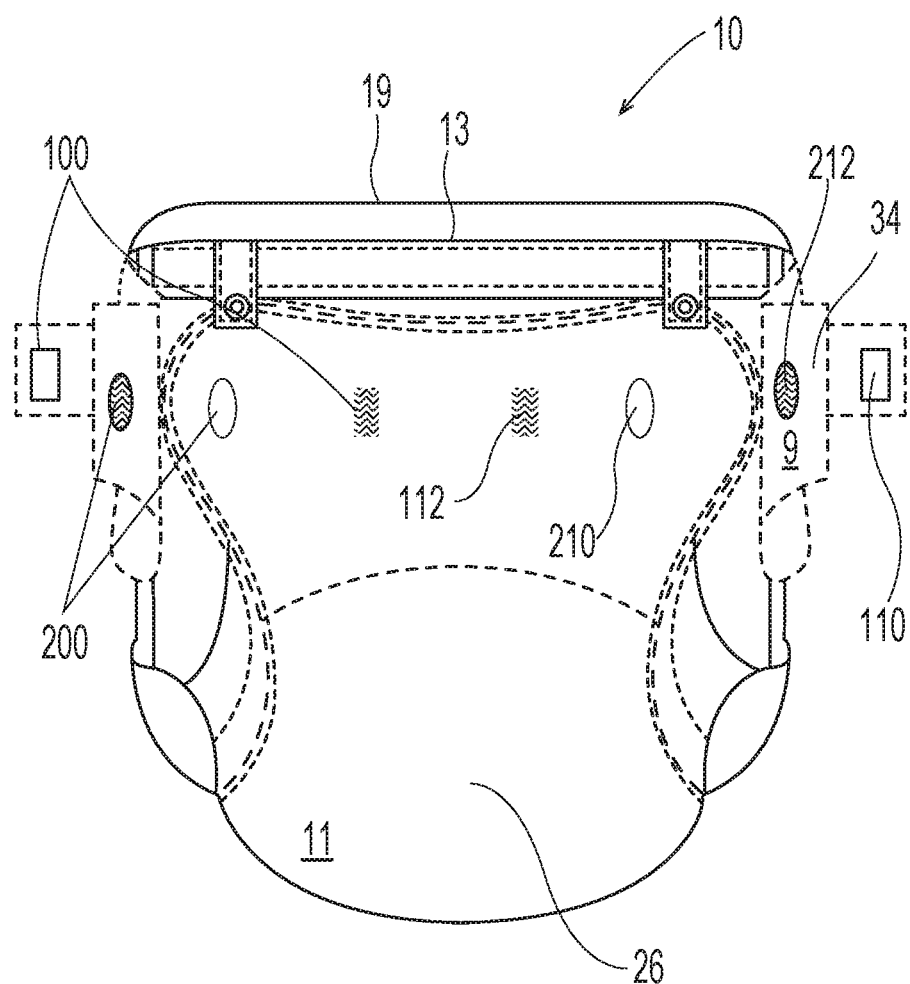
FIG. 2 is a schematic front elevation view of an exemplary absorbent article according to a nonlimiting embodiment. The absorbent article is shown in a folded state.

FIG. 1 is a plan view of an exemplary, nonlimiting embodiment of an absorbent article 10 of the present invention in a flat, uncontracted state. The article may be disposable. The body-facing surface 9 of the absorbent article 10 is facing the viewer. The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article which, when worn, encircle the waist of the wearer. As shown in FIG. 2, the article may comprise a primary fastening system 100 and a secondary fastening system 200 in the waist regions. The fastening systems and surrounding areas are configured to distribute forces and mitigate the effects of tension during wear better than known articles.

Absorbent Article

Returning to FIG. 1, the absorbent article 10 includes a longitudinal centerline 90 and a lateral centerline 95. The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 90. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 95.

The chassis 20 may comprise a liquid permeable topsheet 24, a backsheet 26, and an absorbent core 28 between the topsheet 24 and the backsheet 26. The absorbent core may comprise absorbent material, including for example superabsorbent particles and absorbent gelling materials (AGM). The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 24 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Components of the disposable absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, side panels, leg gasketing systems, superabsorbent, acquisition layers, core wrap materials, adhesives, fastener systems, and land zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

Topsheet

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Nonlimiting examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials (AGM); or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80%, or greater than about 85%, or greater than about 90%, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In nonlimiting examples, two channels are symmetrically disposed about the longitudinal axis. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

Backsheet

The backsheet 26 is generally positioned such that it may be at least a portion of the garment-facing surface 11 of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co. of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing.

Backsheet 26 may also consist of more than one layer. The backsheet 26 may comprise an outer cover and an inner layer. The outer cover may be made of a soft, nonwoven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Extension Elements and Waist Features

Figure 3:
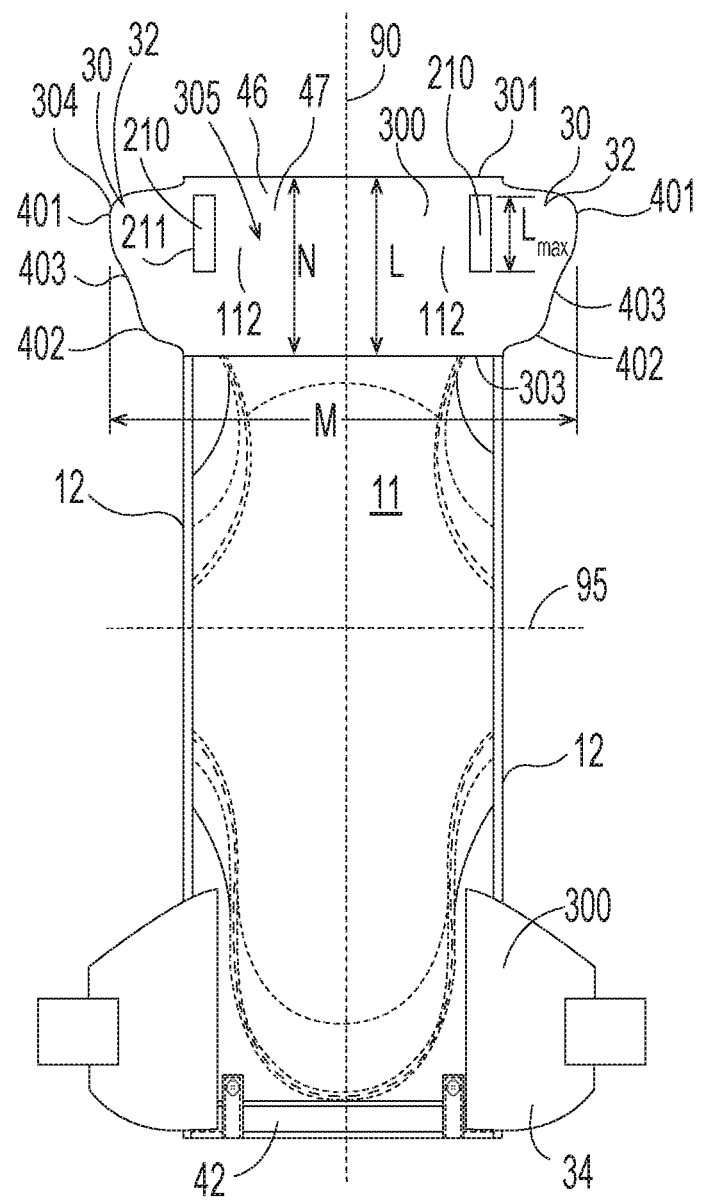
FIG. 3 is a schematic plan view of an exemplary absorbent article according to a nonlimiting embodiment. The absorbent article is shown in a flat, uncontracted state.

The absorbent article 10 may include one or more lateral extension elements 300 (i.e., an element that extends laterally outboard of the longitudinal edge 12 of the chassis). The lateral extension element 300 may be disposed in a waist region. Nonlimiting examples of lateral extension elements include ears 30, belts (which also cover a longitudinally central portion of a waist region), fastener attachment arms 33 (see FIG. 1) and workable combinations thereof. As shown in FIG. 3, the lateral extension element 300 may comprise an outboard lateral edge 301, an inboard lateral edge 303, and an outboard longitudinal edge 304.

In certain embodiments, the article 10 includes one or more lateral extension elements in the form of an ear 30, including for example front ears 32 disposed in the first waist region and/or back ears 34 disposed in the second waist region. An ear 30 may be integral with the chassis or a discrete element joined to the chassis 20. An ear 30 may be extensible or elastic. An ear 30 may be formed from one or more nonwoven webs, woven webs, knitted fabrics, polymeric and elastomeric films, apertured films, sponges, foams, scrims or combinations and/or laminates of any the foregoing.

In some embodiments, an ear 30 may include elastomers, such that the ear is stretchable. In certain embodiments, an ear 30 may be formed of a stretch laminate such as a nonwoven/elastomeric material laminate or a nonwoven/elastomeric material/nonwoven laminate, which also results in the ear being stretchable. The ear 30 may be extensible in the lateral direction of the article. In some embodiments, the ear is elastic in the lateral direction. In further embodiments, the ear 30 may extend more in the lateral direction than in the longitudinal direction. Alternatively, the ear may extend more in the longitudinal direction than in the lateral direction. In certain nonlimiting examples, the ear may include one or more inelastic regions along with a separate elastic region. In some embodiments, the area of the elastic region comprises at least about 20%, or from about 30% to about 80%, of the total area of the ear, reciting for said range every 5% increment therein. An inelastic region may be disposed laterally outboard of an elastic region. In nonlimiting examples, an elastic region is disposed between two inelastic regions.

Any suitable nonwoven may be used in an ear 30. Suitable nonwovens may comprise a basis weight of at least about 8 gsm, or less than about 22 gsm, or about 17 gsm or less, or from about 10 gsm to about 20 gsm, reciting for said range every 1 increment therein. Where the ear 30 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

Nonlimiting examples of suitable elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, strands and the like. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.) and VERSIFY (homopolyolefins and random copolymers, and blends of random copolymers, available from Dow Chemical Company, Midland, Mich.).

The ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example. Alternatively, the ear 30 comprises a gathered laminate, wherein one of the layers is strained to a greater degree than a remaining layer during lamination and/or bonding. In this way, the less extensible layer (i.e., a nonwoven) will form gathers when the laminate is in a relaxed state. Corrugations then form in the nonwoven layer(s) when the subsequently formed laminate is in a relaxed state. The ear may comprise an ultrasonically bonded laminate as is disclosed for example in U.S. Pat. Pub. Nos. 2018/0042777, 2018/0042778; 2018/0271716; and 2018/0271717.

Where an article 10 comprises multiple ears 30, said ears 30 may be the same or may be different. By way of nonlimiting example, a back ear 34 may comprise an elastic ear while a front ear 32 may be inelastic. Additionally, or alternatively, layers of a front ear may be joined by different means than layers of a back ear. For example, the front ear layers may be joined by adhesive, and back ear layers may be joined by ultrasonic bonds.

The absorbent article 10 may comprise a waist feature 40. Waist features 40 may be disposed in the first waist region 14 and/or in the second waist region 18. In some nonlimiting examples, one or both of the article's waist edges 13, 19 may be at least partially defined by a waist feature as illustrated in FIG. 1. In further nonlimiting examples, a waist feature may be disposed inboard of the closest waist edge. A waist feature may be integral with one or more layers of the chassis, cuffs and/or other elements in the waist region, or may be discrete and joined to one or more layers of the chassis, leg cuff structures and/or other elements disposed in the waist region. The waist feature may be joined between layers, on the outward-facing surface 11 of the article, or on the wearer-facing surface 9 of the article. The waist feature may be extensible or elastic. An elasticized waist feature 42 is generally intended to expand and contract to dynamically fit the wearer's waist. Elasticized waist features include waistbands, waist cuffs having pockets formed from a portion of the waist feature that is unattached from the chassis 20, and waist panels and/or belts designed to fit securely about the abdomen of the wearer in diaper, pants or other article configurations. Nonlimiting examples of elasticized waist features are disclosed in U.S. patent application Ser. Nos. 14/533,472; 15/074,675 and 62/855,001. Elasticized waist features may comprise one or more nonwoven layers and one or more elastic elements 45. In nonlimiting examples, the elasticized waist feature comprises elastic strands joined to the nonwoven layer(s). In further nonlimiting examples, the elasticized waist feature comprises a laminate of one or more nonwoven layers and one or more films.

In alternative embodiments, the waist feature may be inelastic. In such configurations, the waist feature may provide additional anchoring about the waist of the wearer.

A waist feature can be used in conjunction with an ear 30 to provide desirable stretch and flexibility, or otherwise enhance fit of the article on the wearer.

In some embodiments, a lateral extension element may be in the form of a belt such that it also constitutes a waist feature. The lateral extension element 300 may comprise a combination belt structure 46, formed from a web material 47, which extends through the waist region and laterally outboard of the longitudinal edges of the chassis as shown in FIG. 3 for example. By combination belt structure 46, it is meant that the element is configured to both (i) provide and/or support a receiving component of a fastening system (discussed below) and (ii) form one or more ears 30 that extend outboard of a longitudinal edge 12 of the chassis. In the nonlimiting example shown in FIG. 3, the combination belt structure 46 is configured to provide and/or support primary receiving components 112 as well as secondary fastening components 210, each of which is discussed below.

Without being bound by theory, it is believed that the combination belt structure prevents waste and reduces manufacturing costs and complexity as compared to ears. For example, known absorbent articles include front ears formed from extensions of one or more of the backsheet and topsheet materials, or alternatively, separate sections of material bonded to one or more of the topsheet, backsheet and/or cuff structure so as to extend laterally from the left and right sides of the chassis. Where the front ears are extensions of one or more of the backsheet and topsheet materials, manufacturing necessarily includes a profiled cutting of these materials to provide the extending front ear portions, and associated material waste. When the front ears are formed of separate sections of material bonded to one or more of the topsheet, backsheet and/or cuff structure, manufacturing must include steps associated with placing and bonding these front ear components to the chassis. As an alternative, however, a section of web material 47 used to form a primary receiving component 112 of a primary fastening system may be selected so as to also to be suitable to form and provide one or more front ears 32, when cut to a size which allows for the section of web material to extend laterally beyond the chassis along the longitudinal side(s). In one example, the section of web material may be a section of nonwoven web material adapted to fastenably engage hooks included as or with primary fastening components 110, and thereby serve as the loops receiving component 112 of a hook-and-loop primary fastening system. In a more particular example, the section of nonwoven web material may be pattern bonded in a pattern of thermal bonds configured to enhance the strength and reliability of the material, and of the loops structures it provides. Suitable pattern bonding is disclosed in U.S. patent application Ser. No. 16/575,424. Not only does the combination belt structure provide a dual use as described, but the inclusion of the web material 47 to supplement the other materials of the chassis provides apparent and actual added lateral tensile strength, bending resistance, caliper and robustness to the waist region.

In certain embodiments, the combination belt structure 46 may comprise a maximum longitudinal length, N, of about 30 mm to about 100 mm, or from about 35 mm to about 90 mm, or from about 40 mm to about 85 mm, reciting for each range every 1 mm increment therein. The combination belt structure may comprise a maximum lateral width, M, from about 100 mm to about 500 mm, or from about 150 mm to about 400 mm, or from about 180 mm to about 300 mm, reciting for each range every 1 mm increment therein.

Figure 4:
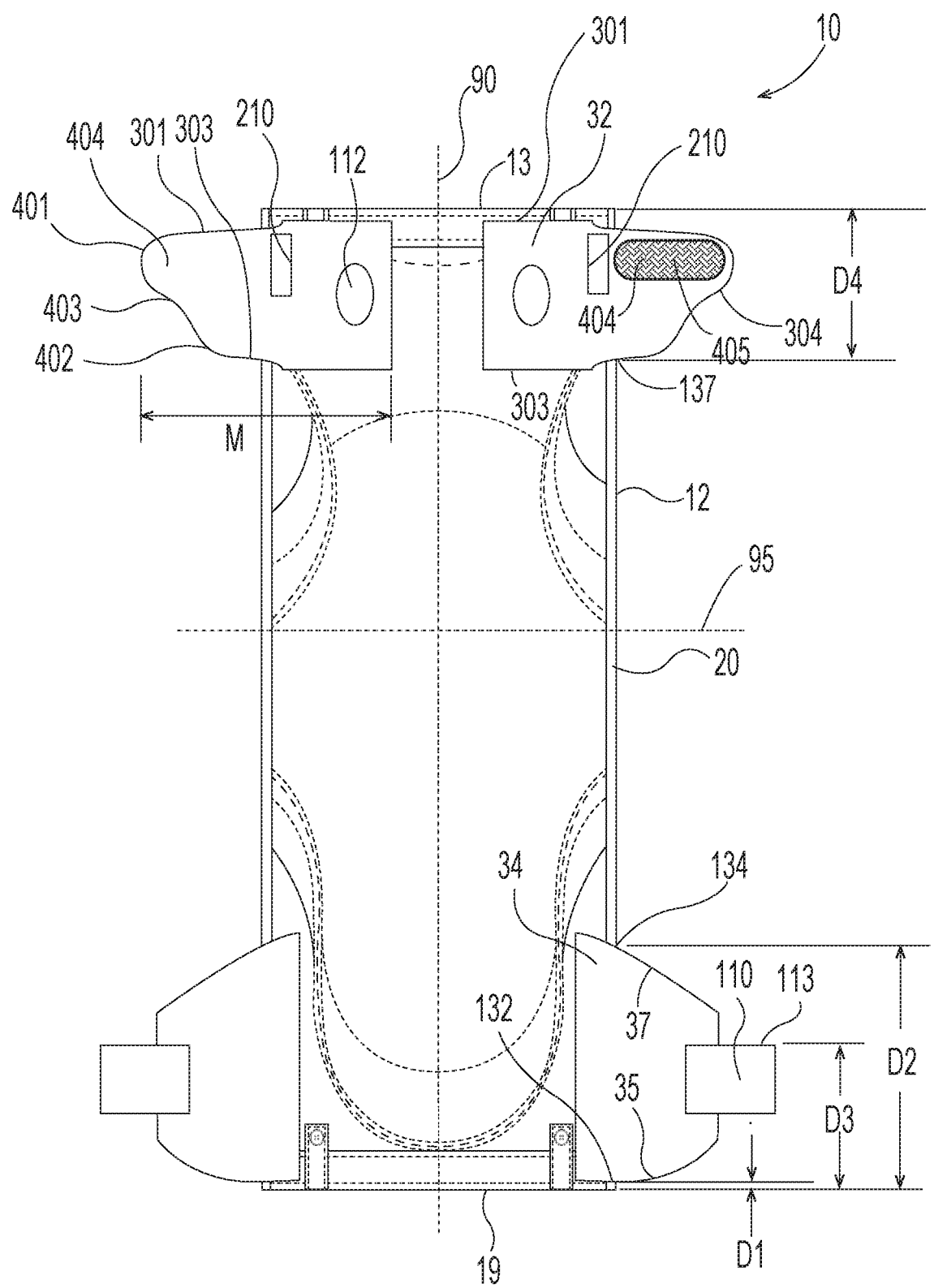
FIG. 4 is a schematic plan view of an exemplary absorbent article according to a nonlimiting embodiment. The absorbent article is shown in a flat, uncontracted state.

In some examples shown in FIG. 4, two discrete sections of web material 47 may be used to provide respective left and right front ears 32 and provide or support respective left and right primary receiving components 112. In some circumstances, this configuration may simplify and/or reduce costs of manufacturing. For the avoidance of doubt, the discrete sections comprise a combination belt structure as they each provide support for a primary receiving component and form an ear.

An ear, including an ear portion of a combination belt structure, may be configured to have curvilinear edges. In nonlimiting examples, an inboard lateral edge 303 has a concave curvature in the front ear portion laterally outboard of the chassis. Such a curvature may provide for a comfortable and/or visually attractive fit of the diaper about the wearer, at the hip areas. Such a curvature may be accompanied by a curvature of the outboard lateral edge 301 having a profile that is parallel to that of the inboard lateral edge 303, which allows for nesting of shapes for the section(s) of web material 47 during manufacturing, enabling maximum usage of the web material component and/or minimization of waist.

Further to the above, when the ear is provided as a portion of a combination belt structure 46, the belt 46 may be adapted to be fit the complex geometry that includes both the front waist area and about the hip and upper thigh region of the wearer. In certain embodiments, the combination belt structure 46 may have a varying width throughout at least a portion of its longitudinal length. A longitudinal edge 304 may comprise a curvilinear shape as shown for example in FIGS. 3 and 4. The curvilinear shape may have at least two convexities 401 and 402 and at least one concavity 403 disposed intermediate the two convexities. The convexities may be disposed at different lateral positions, such that one is more laterally inboard relative to the other.

In some embodiments, one convexity 401 may be disposed both laterally outboard and longitudinally outboard of the other convexity 402. In embodiments where the article (or belt) comprises two ears disposed on opposite lateral sides, each ear may comprise two convexities with one concavity therebetween. In such embodiments, the lateral distance between the two longitudinally outboard convexities 401 may be greater than the lateral distance between the two longitudinally inboard convexities 402. Without wishing to be bound by theory, it is believed these embodiments allow the belt to fit smoothly into the body's complex geometry and provides a more comfortable wearing experience by allowing the wearer's legs to move with less hindrance from material (i.e., the belt is narrower near the upper thighs) while maintaining a secure fit around the waist. In addition, minimizing the amount of material proximate to the inboard edge reduces the likelihood of the material folding over when positioned beneath the back ear during application, and thereby increases fit and comfort.

The ear 32 may comprise a grip portion 404, as shown in FIG. 4. The grip portion 404 is an area of the ear that may be used to pull the front ear flat while wrapping the second waist region about the wearer to fasten. In certain embodiments, the grip portion is located closer to the outboard lateral edge 301 of the ear than the inboard lateral edge 303. The ear may be configured to identify the grip portion. In nonlimiting examples, the ear (or combination belt structure that comprises the ear) comprises its largest width at a convexity 401, as shown in FIGS. 3-4. Without being bound by theory, it is believed that such configuration intuitively indicates an area suitable for a thumb and/or finger grip. Additionally, or alternatively, the grip portion 404 may be provided with a signal 405 to distinguish the area from the remaining ear. The signal may comprise a color, a texture, pattern (e.g., bond pattern), and/or indicia (e.g., words, logos, trademarks).

Fasteners

Returning to FIG. 2, the absorbent article 10 may also include a primary fastening system 100. When fastened, the primary fastening system 100 interconnects the first waist region 14 and the rear waist region 18 resulting in a waist circumference that may encircle the wearer during wear of the absorbent article 10.

One or more portions of the fastening system may be formed from, or may be joined to, a lateral extension element 300. Additionally, or alternatively, portions of the fastening system may be formed from, or may be joined to, the chassis 20. In embodiments where the portions of the fastening system are joined, said portions may be joined to an exterior surface or between layers. In embodiments where portions of the fastening system are integral, said portions may be integral with any suitable surface.

The primary fastening system may comprise a primary fastening component 110, such as hooks, disposed in the second waist region 18. The primary fastening component 110 may be discrete, such as a discrete patch of fastening material joined to the chassis or joined to another component in the second waist region. In nonlimiting examples, the primary fastening component is joined to an ear 34 or a separate layer joined to the ear. In another nonlimiting example, the primary fastening component may be integral with an ear. In further nonlimiting examples, the primary fastening component 110 may be integral with the chassis and/or another component joined to the chassis.

In some embodiments, the primary fastening component 110 may be separately applied sections or patches of hooks material that are bonded to a back ear or chassis by heat, compression, adhesive, ultrasonic bonding or any combination thereof. In other examples, a primary fastening component may be a patch of hooks that are formed directly on a section of the ear, more particularly formed directly on a section of a polymeric layer of nonwoven. For example, the hooks may be produced via application of molten polymer resin onto the layer, and subsequent formation of hooks in and from the melted, applied resin via known methods. The primary fastening components may be integrally formed from polymeric material by heating and softening a portion of the material and pressing it into hook-forming cavities, as is disclosed in U.S. Pat. No. 8,784,722. The primary fastening components may be integrally formed from the polymeric material through a single continuous process as is disclosed in commonly assigned U.S. patent application Ser. No. 16/545,425.

Still referring to FIG. 2, the primary fastening system 100 may further comprise a primary receiving component 112, such as loops, disposed in the first waist region 14. The primary receiving component may be discrete, such as a discrete patch of receiving material joined to the chassis or joined to another component in the first waist region. In other embodiments, the primary receiving component may be integral with the chassis or integral with another component in the first waist region. In such embodiments, the backsheet, a combination belt structure 46, an ear 30 or combinations thereof may comprise material, such as loop material, which may form the primary receiving component.

The primary receiving component is operatively engageable with the primary fastening component such that the primary fastening system secures the article about the waist and/or hip of the wearer. Nonlimiting examples of engageable fastening and receiving components include tape tabs, hook and loop fastening components, interlocking fasteners such as tabs & slots, buckles, buttons, snaps, and/or hermaphroditic fastening components. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The primary fastening component and/or the primary receiving component may further include a release tape or other material that protects the component from insult prior to use. In nonlimiting examples, the primary fastening component and/or the ear is foldable and may be folded prior to use such that the primary fastening component engages with material (e.g., ear material) that protects it from insult.

The primary components 110, 112 may each be any suitable shape or size. The primary components 110, 112 may be disposed on opposite surfaces of the article. For instance, the primary fastening component 110 may be disposed on the wearer-facing surface 9 of the article and the primary receiving component may be disposed on the garment-facing surface 11. While shown in the waist region, it is also contemplated that one or both of the primary components 110, 112 may be disposed in any portion of the diaper, which may facilitate closing or wrapping the article during disposal, securing the article to itself and/or securing the article to another surface such as a garment.

The article may also comprise a secondary fastening system 200. The secondary fastening system 200 may comprise a secondary fastening component 210 and a secondary receiving component 212 that are operatively engageable to further secure the article about the wearer. The secondary fastening component 210 may be disposed in the first waist region, and the secondary fastening receiving component 212 may be disposed in the second waist region. Addition of a secondary fastening system can provide a greater surface area for fastening, and thereby de-concentrate lateral tensile forces communicated through the fastening location(s) as the rear waist region is pulled toward the front waist region, and vice versa, when the diaper is worn. In addition, having two distinct fastening locations reduces the tendency of the front portion of the article to pivot (i.e., pivot around the single fastening location of the primary fastening system). Further, the secondary system helps to create a line of tension closer to the front waist edge, which may reduce the likelihood of folding or flipping over of the front waist edge during wear. Further still, the secondary system may create an anchoring geodesic to direct forces from the crotch region to over the hips in order to prevent sagging during wearer. The secondary system may also help to secure the front ear or combination belt structures in place during wear. Each of the foregoing can serve to provide for more effective and durable fastening and less longitudinal and/or lateral flexing, sagging and/or wrinkling of the diaper materials about the fastening areas during wear.

The secondary components 210, 212 may be disposed on opposite surfaces (e.g., the secondary fastening component may be disposed on the garment-facing surface 11 and the secondary receiving component may be disposed on the wearer-facing surface 9). The secondary fastening system may comprise any of the features detailed above with respect to the primary fastening system. A secondary component may be discrete from the chassis or another feature in the respective waist region, or the secondary component may be integral with the chassis or another feature joined to the chassis of the respective waist region and may form a portion of a surface of the chassis or said feature.

In a particular example, secondary fastening components 210 may be patches of hooks, and material disposed on and/or forming the wearer-facing sides of the back ears 34 may be, or include, material that serves as the loops component of a hook-and-loop fastening system. In one particular example, a wearer-facing layer forming a portion of the rear waist region may include a nonwoven material adapted to serve as a receiving component 212 and fastenably engage with hooks constituting the secondary fastening components 210. As described above with respect to the primary fastening component, the secondary fastening component may be a separate patch of material joined to the chassis or another component in the first waist region, such as a web material that forms a combination belt structure or a web material that does not provide ears but may provide just the secondary fastening component or both the primary receiving component and the secondary fastening component. Alternatively, a portion of the secondary fastening component may be integral with the chassis or said other component that is disposed in the first waist region. As noted with the primary fastening component, the secondary fastening component may be produced via application of molten polymer resin onto the web material, and subsequent formation of hooks in and from the melted, applied resin via known methods. The secondary fastening components may be integrally formed from polymeric material by heating and softening a portion of the material and pressing it into hook-forming cavities, as is disclosed in U.S. Pat. No. 8,784,722. The secondary fastening components may be integrally formed from the polymeric material through a single continuous process as is disclosed in commonly assigned U.S. patent application Ser. No. 16/545,425. Further, while shown in the first waist region, it is also contemplated that one or both of the secondary components 210, 212 may be disposed in any portion of the diaper, which may facilitate closing or wrapping the article during disposal, securing the article to itself and/or securing the article to another surface such as a garment.

It may be desired to cut or otherwise impart at least the lower edges of secondary fastening components with rounded profiles, or profiles other than 90 degree corners, rather than sharp corners as in the rectangular shape as depicted in the figures. This may be desirable for purposes of reducing chafing of the wearer's skin that might otherwise occur, through localized concentrations of pressure against the wearer's skin at sharp corners of components 210. Thus, it may be desired that, for example, patches of hooks material constituting secondary fastening components 210 have a circular, oval, elliptical, rounded rectangle or other shape lacking sharp corners, at least on the edges of the lower half of the length thereof.

In some embodiments, the primary and secondary fastening components are disposed on opposite surfaces (e.g., the primary fastening component is disposed on the wearer-facing surface and the secondary fastening component is disposed on the garment-facing surface). Likewise, the primary and secondary receiving components may be disposed on opposite surfaces.

In nonlimiting examples, the web material comprising the secondary fastening component (e.g., hooks) may also comprise the primary receiving component (e.g., loops). Additionally, or alternatively, the polymeric material comprising the primary fastening component (e.g., hooks) may also comprise the secondary receiving component (e.g., loops). In such nonlimiting examples, said substrates (i.e., the web material, the polymeric material) may comprise a first constraint, where in any identifiable linear path along the section of material that:

(a) has a width greater than 2 mm; and
(b) forms an angle of 45 degrees or less with the machine direction, in x-y plane along a major surface of the section of material, at least partially overlies a bond or bonds in the pattern at a plurality of locations along the path. In some further nonlimiting examples, the substrate may also comprise a second constraint, where the maximum identifiable dimension between locations at which bonds are overlaid by any such path is from 1 mm to 12 mm, more preferably from 2 mm to 10 mm, and even more preferably from 2 mm to 8 mm.

Further to the above, integral fastening components may be formed with varying directionality to provide different benefits in different sections of the component. For instance, hooks which are asymmetric about their vertical centerline (such that create an inverted J-shape or similar hook configuration) may be formed so that the open portion is pointed in the direction of expected engagement. In further nonlimiting examples, hooks in a front waist region 14 may be imparted with directionality approaching or along the lateral direction and extending toward the longitudinal axis of the diaper. Such directionality provides mechanical structure extending in a direction opposite the ordinary direction of shear forces (directed away from the longitudinal axis in the front region) that would be exerted on the hooks in that region while the hooks are engaged during wear, providing for added fastening strength and/or more secure attachment, as compared with non-directional hooks of similar size, material utilization (shape volume) and numerical density. Hooks in the rear waist region may be imparted with directionality toward the longitudinal axis of the diaper (when the fastening member is in the open position). Such directionality would oppose the ordinary direction of shear forces that would be exerted on the hooks in the front waist region when the hooks are engaged (i.e., fastened) during wear, providing for added fastening strength and/or more secure attachment, as compared with non-directional hooks of similar size, material utilization (shape volume) and numerical density.

Positioning of Fastening Components

In certain embodiments, a fastening component may be longitudinally offset from a lateral edge of the component on which the fastening component is disposed. In an embodiment shown in FIG. 3 for example, the secondary fastening component 210 may be longitudinally offset from an outboard lateral edge 301 of a lateral extension element by at least about 1 mm, or at least about 3 mm, or at least about 5 mm, or from about 1 mm to about 10 mm, reciting for said range every 0.5 mm increment therein. In nonlimiting examples, a fastening component does not coincide with any lateral edge 301, 303 of the component to which it is attached. It may be desired, for example, that each secondary fastening component 210 is disposed with its surface area and outer edges entirely within the surface area and outer edges of the lateral extension element, or other article component, to which it is joined.

The fastening component may have a maximum longitudinal length, $L_{max}$, that is less than the longitudinal length of the component, L, on which the fastening component is disposed, in an area of attachment 305. For instance, a secondary fastening component may be disposed on a combination belt structure 46 and have a maximum longitudinal length, $L_{max}$, that is less than the average length of the belt 46 in the area of attachment 305. $L_{max}$, may be about 95% or less, or 90% or less, or 85% or less, or from about 25% to about 95%, or from about 50% to about 90% of L, or from about 60% to about 85% or L, reciting for said range every 1% increment therein. Additionally, or alternatively, $L_{max}$, may be less than L by at least about 10 mm, at least about 15 mm, or from about 10 mm to about 50 mm, or from about 10 mm to about 30 mm, or from about 10 mm to about 15 mm, reciting for each range every 1 mm increment therein. Without being bound by theory, it is believed that offsetting the fastening component from a lateral edge prevents exposing the fastening component to a wearer's skin. Tension on areas of the article may result in folding or collapsing of materials surrounding the fastening component. By positioning the fastening component away from an edge, folding and collapsing is less likely to result in exposing the fastening elements to the skin. In other words, the material would be required to deform more before such exposure could occur.

Additionally, or alternatively, a fastening component may be laterally offset from a longitudinal edge of a component on which it is disposed. For instance, an outboard edge 211 of a secondary fastening component 210 may be laterally inboard of a longitudinal edge 304 by at least about 1 mm, or at least about 3 mm, or at least about 5 mm, or from about 1 mm to about 10 mm, reciting for said range every 0.5 mm increment therein. In nonlimiting examples, the outboard edge 211 of the secondary fastening component may be laterally inboard of a chassis edge 12.

To maximize the likelihood that the secondary fastening component 210 will be covered, and otherwise will be unlikely to come into undesirable contact with the wearer's skin during wear, it may be desired to locate the secondary fastening component 210 in a suitable location along the longitudinal direction relatively other portions of the article, such as the position of the back ear 34 and/or the primary fastening component 110.

Referring to FIG. 4, a back ear 34 has an outboard lateral edge 35 and an inboard lateral edge 37. Outboard lateral edge 35 meets longitudinal edge 12 of the chassis 20 at a first intersection point 132. Inboard lateral edge 37 meets longitudinal edge 12 of the chassis at a second intersection point 134. The second intersection point 134 lies distance D2 from the rear waist edge 19. First intersection point 132 lies a distance D1 from the rear waist edge 19. When the back ears 34 are integral extensions of one or more of the topsheet and backsheet, for purposes herein the first intersection point 132 lies at the intersection of the rear waist edge 19 and a line perpendicular to the front waist edge and tangent to the longitudinal edge 12 where the article not including front ears 32 is widest forward of lateral axis 95. Similarly, the second intersection point 134 lies at the intersection or meeting of the inboard edge 37 with the line just described. The secondary fastening component 210 be longitudinally located entirely between distances D1 and D2, from the front waist edge 13. When the fastening members are suitably shaped, such longitudinal location can help ensure that secondary fastening component 210 will be entirely covered by the back ear 34 when the diaper is fastened about a wearer for which the diaper is sized.

Still referring to FIG. 4, an inboard intersection point 137 of the inboard lateral edge 303 of the lateral extension element 300 and the chassis may be located a distance D4 from the front waist edge 13. It may be desired that secondary fastening component 210 be located entirely outboard of the inboard lateral edge 303. It may further be desired that the secondary fastening component 210 be located at a distance from the front waist edge 13 that is entirely less than distance D4 from the front waist edge 13. Such a location will help ensure that a portion of the lateral extension element 300 is available to provide shielding and cushioning for the wearer's skin, against possible irritation that may be caused by the lower edges of secondary fastening component 210.

It may also be desired that secondary fastening component 210 be located closer to the outboard lateral edge 301 than to the inboard lateral edge 303 of a lateral extension element. This may be generally desired so as to locate the secondary first components as close the front waist edge 13 as practical, so as to help minimize or avoid flipping over of portions of the chassis proximate the front waist edge 13, when the diaper is worn.

An inward-most extent 113 of the primary fastening component 110 is located a distance D3 from the rear waist edge 19. It may be desired that distance D3 be less than distance D4. This will help ensure that a portion of the lateral extension element is disposed below the primary fastening component 110 when the article is fastened and worn, thereby providing shielding and cushioning for the wearer's skin, against possible irritation that may be caused by the lower edges of the fastener. This may be particularly desirable in a situation in which a caregiver desires to fit the diaper as loosely on the wearer as possible, by, e.g., affixing the primary fastening component 110 to the front ear 32, laterally outboard of the longitudinal edge of the chassis 12—rather than at a more laterally inward location on the front waist region.

Areas of Attachment

Figure 5:
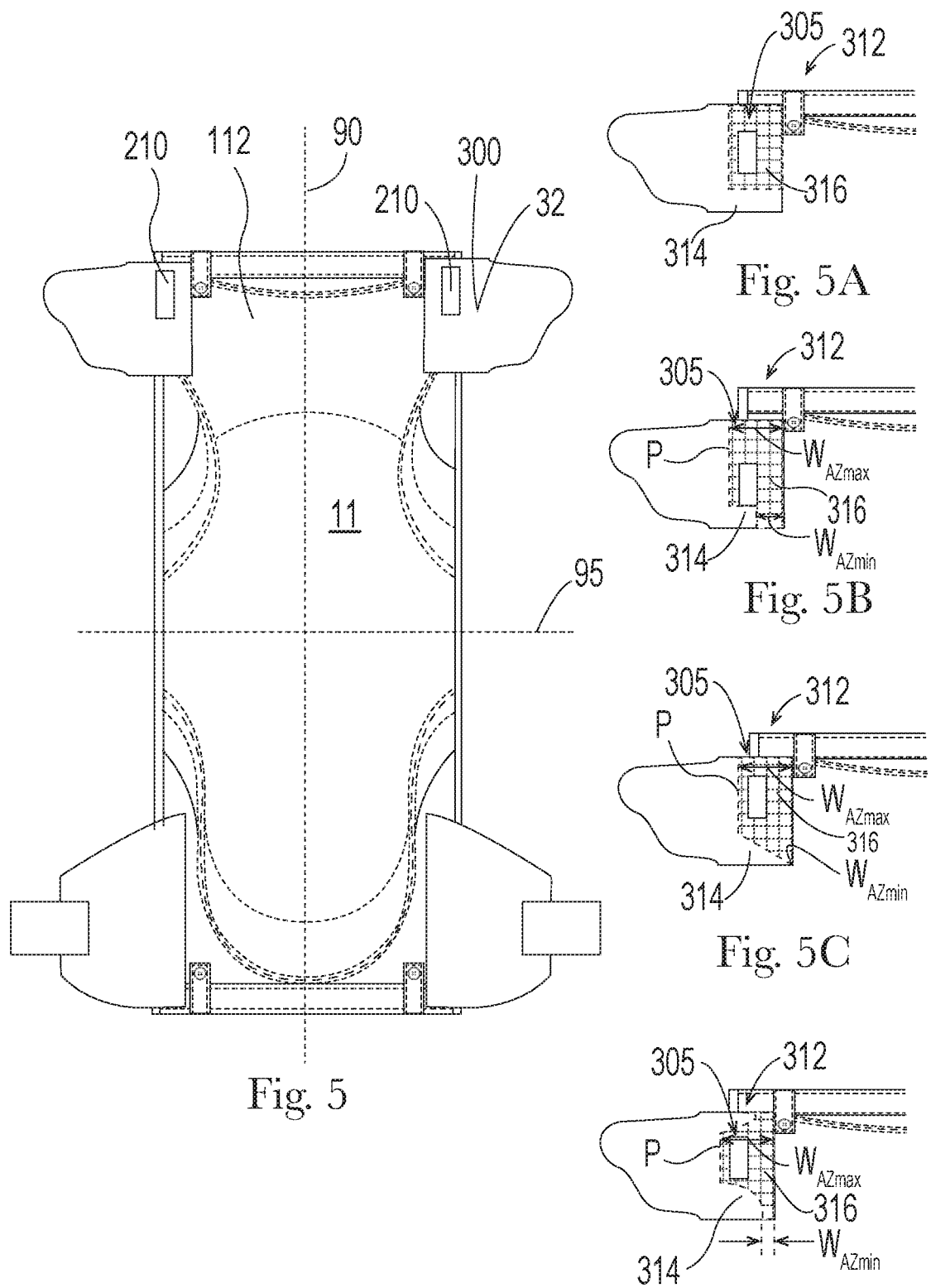
FIG. 5 is a schematic plan view of an exemplary absorbent article according to a nonlimiting embodiment. The absorbent article is shown in a flat, uncontracted state.

The article may further comprise attachment zones and/or patterns which reduce the effects of the tension experienced by portions of the article during use. FIG. 3 schematically depicts the garment-facing side 11 of an absorbent article having a lateral extension element 300 (more specifically a combination belt structure 46) disposed in the first waist region. FIGS. 3A-3D show embodiments of the first waist region schematically with layer(s) of the belt-chassis composite 312 removed to reveal exemplary areas of attachment 305. Similarly, FIG. 5 schematically depicts the garment-facing side of an absorbent article having a lateral extension element 300 (more specifically an ear 32) disposed in the first waist region. FIGS. 5A-5D show embodiments of the first waist region schematically with layer(s) of the ear-chassis composite 312 removed to reveal exemplary areas of attachment 305.

It is to be understood that the composite 312 may comprise any suitable layers of the article including for example, layers of the chassis such as the topsheet-backsheet laminate, layers of an ear 30, layers of a combination belt structure 46 and combinations thereof. The area of attachment 305 is the area wherein composite layers are combined together. The area of attachment 305 may be formed by any suitable means including adhesive, mechanical bonding, pressure bonding, ultrasonic bonding, and combinations thereof. The attachment may be in the form of discontinuous bonds (e.g., point bonds, lattice bonding, spiral bonds) or continuous bonding (e.g., continuous slot coating).

The area of attachment may comprise an anchoring zone 316 and a decoupled zone 314. In the decoupled zone, the composite 312 is unattached or attached in a weaker or more flexible manner than in the anchoring zone.

Figure 6:
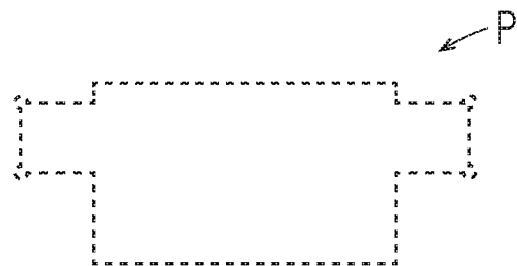
FIG. 6 is a schematic depiction of an exemplary perimeter of an anchoring zone according to a nonlimiting embodiment.
Figure 6A:
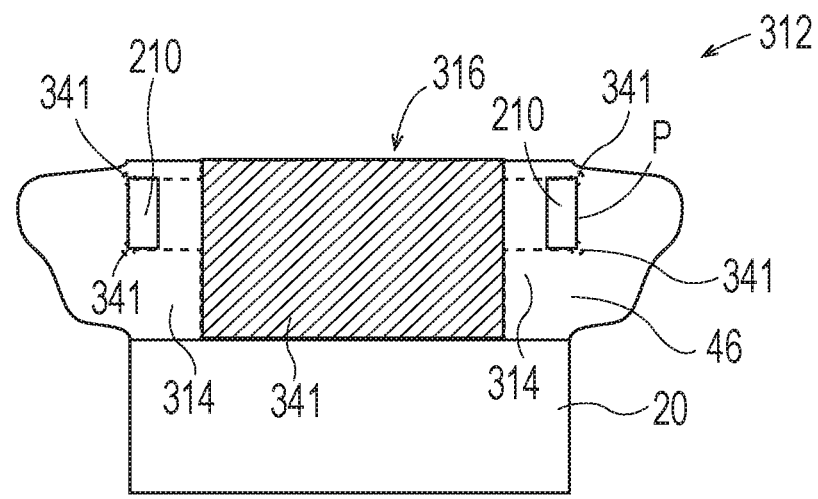
FIGS. 6A-6B are schematic plan views of exemplary composites with bond sites revealed to illustrate nonlimiting examples of an anchoring zone having the perimeter shape of FIG. 6.
Figure 6B:
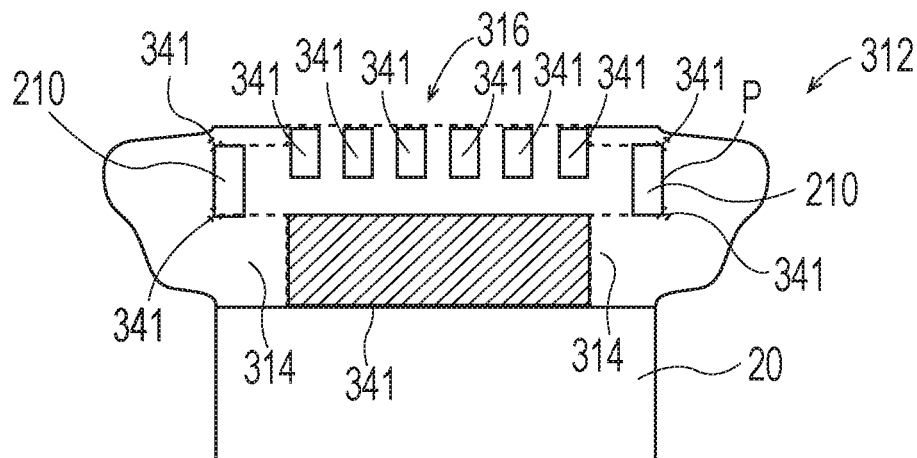
Figure 7:
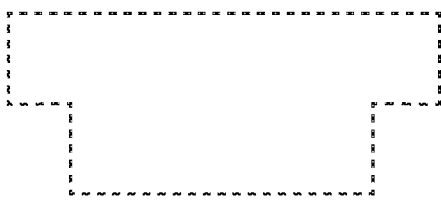
FIG. 7 is a schematic depiction of an exemplary perimeter of an anchoring zone according to a nonlimiting embodiment.
Figure 7A:
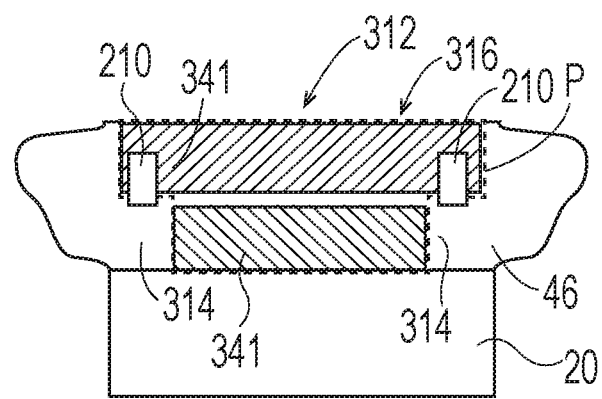
FIGS. 7A-7C are schematic plan views of exemplary composites with bond sites revealed to illustrate nonlimiting examples of an anchoring zone having the perimeter shape of FIG. 7.
Figure 7B:
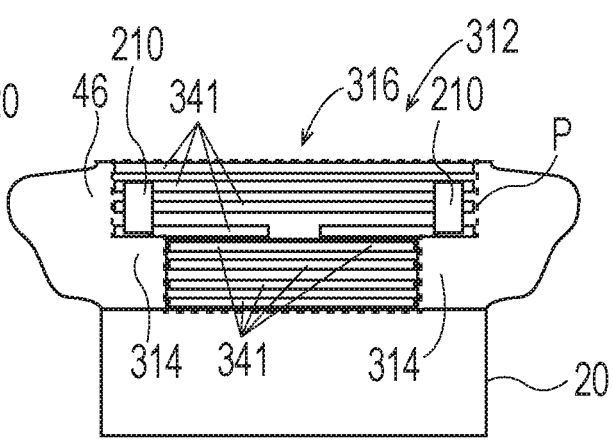
Figure 7C:
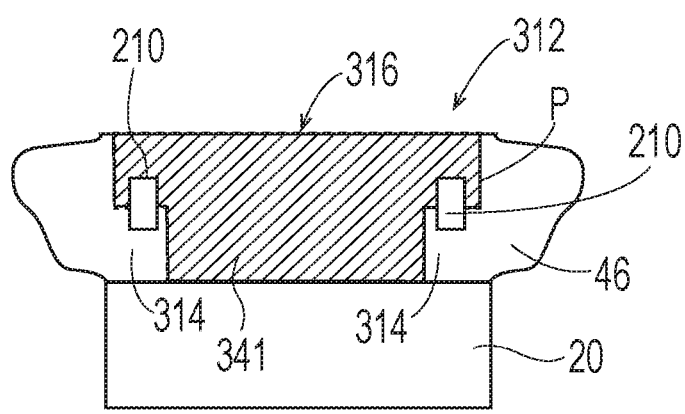

The anchoring zone 316 may comprise continuous or discontinuous bonding, formed by adhesive, ultrasonic bonds, thermal bonds, compression bonding and any combination thereof. The anchoring zone 316 may be defined by a perimeter P. The perimeter P separates the decoupled zone from the anchoring zone. In embodiments involving discontinuous bonding, the perimeter P is defined by connecting, via imaginary lines, outermost anchoring bond sites 341, as shown by the dotted line in FIGS. 6-8B for example. An outermost anchoring bond site is one that is closest to a lateral edge of the composite 312 at a given longitudinal position as compared to remaining anchoring bond sites or closest to a longitudinal edge of the composite at a given lateral position as compared to remaining bond sites. FIG. 6 illustrates a perimeter, and FIGS. 6A-6B illustrate embodiments of anchoring zones on chassis-lateral extension elements, each of which comprise the perimeter shape in FIG. 6. Likewise, FIGS. 7A-7D illustrate embodiments of anchoring zones on chassis-lateral extension elements, each of which comprise the perimeter shape in FIG. 7. And FIGS. 8A-8B illustrate embodiments of anchoring zones on chassis-lateral extension elements, each of which comprise the perimeter shape in FIG. 8. The perimeter P may comprise substantially straight portions, curvilinear portions or combinations thereof. Straight portions may be at angle of 5-89° with respect to the lateral or longitudinal axis.

Returning to FIGS. 5B-5D, the anchoring zone 316 may comprise a varying width. The anchoring zone 316 may comprise a maximum width, $W_{AZmax}$, and a minimum width, $W_{AZmin}$. Widths are measured to the nearest 0.05 mm along a line parallel to the lateral axis. In certain embodiments, the maximum width, $W_{AZmax}$, may be at least about 10% or greater, or at least about 15% greater, or at least about 20% greater, or from about 10% to about 100% greater, or from about 20% to about 80%, or from about 25% to about 75% greater than the minimum width, $W_{AZmin}$, reciting for each range every 5% increment therein. It is also contemplated that the minimum width may be 0, and the zone may narrow to a point at the minimum width as shown in FIG. 5C. The maximum width of the anchoring zone may be disposed in an area that is longitudinally outboard of an area having the minimum width.

Figure 3A:
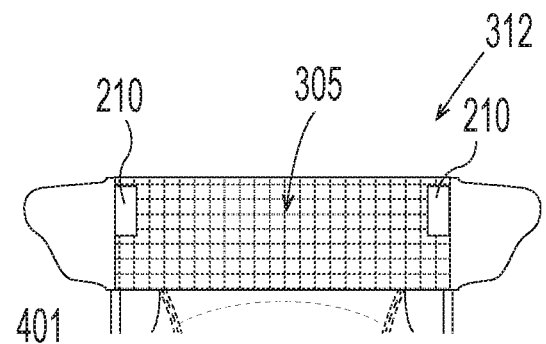
FIGS. 3A-3D are schematic plans views of nonlimiting embodiments of one of the waist regions of FIG. 3 with layer(s) removed to reveal nonlimiting examples of areas of attachment.
Figure 3B:
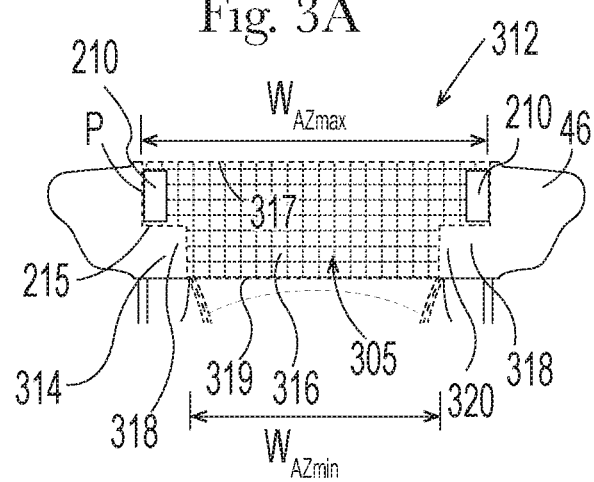

Referring to FIG. 3B, the decoupled zone may comprise an area of detachment 318, wherein two or more layers of the composite are unattached. In nonlimiting examples, one or more layers of a combination belt structure 46 are detached from the chassis in the decoupled zones. In further nonlimiting examples, one or more layers of an ear 32 are detached from the chassis in the decoupled zones.

In further embodiments, the decoupled zone may comprise zone of weakness 320, wherein the two or more layers of the composite are bonded and comprise an Average Peel Force that is at least 50% less than the Average Peel Force of the same layers in the anchoring zone 316 of the composite, as determined by the Peel Force Test Method herein. In certain embodiments shown in FIG. 3D, the decoupled zone may comprise an area of extensibility 322, wherein the composite may extend by at least 15%, or at least 20%, or at least about 25% more than the anchoring zone 316, without rupture or break, according to steps 1-5(a) of the Hysteresis Test herein, replacing 100% strain with 50% (i.e., $l_{max}-l_{ini}$ for the decoupled zone may be at least 15%, etc., greater than $l_{max}-l_{ini}$ of the anchoring zone, where $l_{max}$ is the stretched length or the length at break if applicable). The area of extensibility may be formed by, for example, activating the composite in the said area. One suitable activation process is disclosed in U.S. Pat. No. 5,156,793. During the activation process, one or more layers of the composite are plastically deformed thereby weakening said layer(s) and increasing their extensibility.

The decoupled zone may comprise any suitable shape or size including rectangular, triangular, curvilinear and combinations thereof. The decoupled zone may comprise any combination of areas of detachment, zones of weakness and/or areas of extensibility.

Figure 3C:
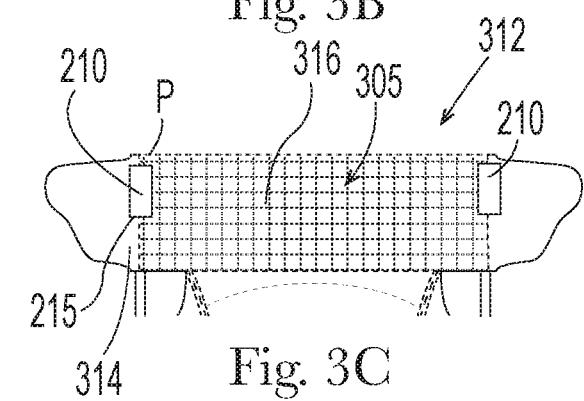
Figure 3D:
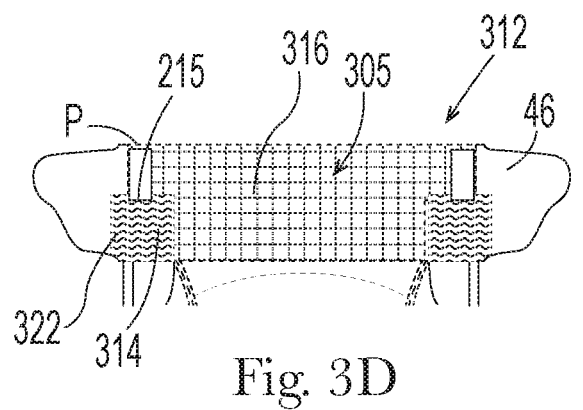

A portion of the decoupled zone may be disposed laterally outboard of the anchoring zone as shown in FIG. 3C for example. Additionally, or alternatively, a portion of the decoupled zone 314 may be disposed longitudinally inboard of the secondary fastening component 210 as shown in FIG. 3B for example. Further, in some embodiments, a portion of a combination belt structure is disposed longitudinally inboard of the inboard lateral edge 215 of the secondary fastener.

The secondary fastening component 210 may be at least partially disposed in the anchoring zone 316, thereby helping to ensure the secondary fastening component is fixed in the desired position during application and wear. In nonlimiting examples, at least about 10%, or at least about 20%, or at least about 25%, or at least about 30%, or from about 10% to about 100%, or from about 25% to about 100% of the area of the secondary fastener is located within the anchoring zone, reciting for each range every 5% increment therein. If the secondary fastening component fully overlies a decoupled zone, said fastening component may be more prone to movement, allowing for an edge and/or the surface of the component to contact the skin. By reducing the overlap between the secondary fastening component and the decoupled zone, flexibility may be achieved without increasing the likelihood of skin irritation.

Figure 7D:
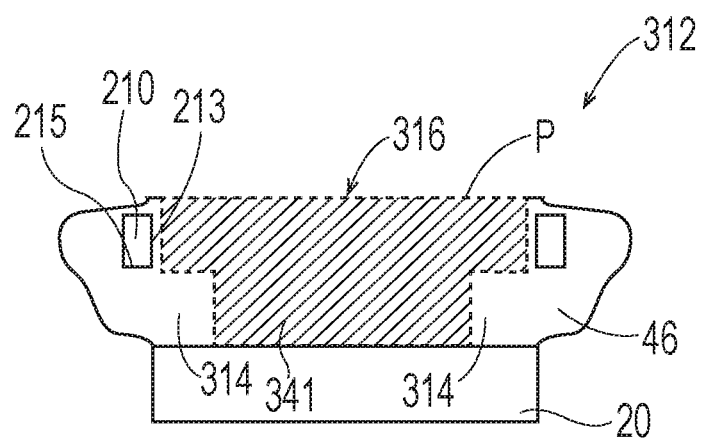
FIG. 7D is a schematic plan view of an exemplary composite with bond sites revealed to illustrate a nonlimiting example of an anchoring zone.
Figure 8:
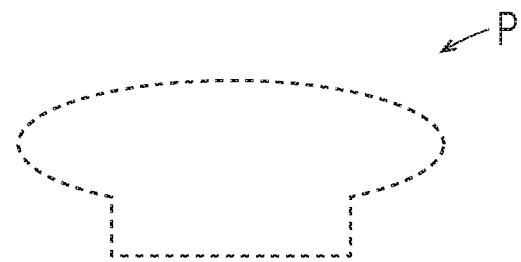
FIG. 8 is a schematic depiction of an exemplary perimeter of an anchoring zone according to a nonlimiting embodiment.
Figure 8A:
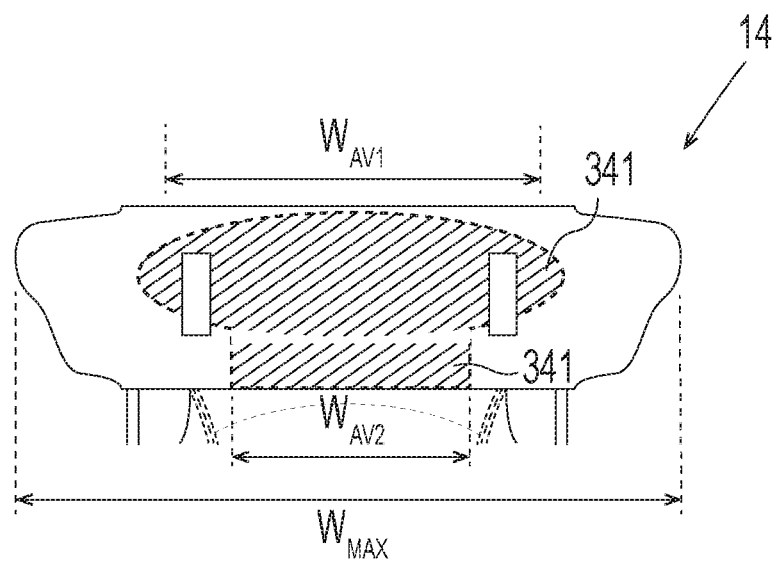
FIGS. 8A-8B are schematic plan views of exemplary composites with bond sites revealed to illustrate nonlimiting examples of an anchoring zone having the perimeter shape of FIG. 8.
Figure 8B:
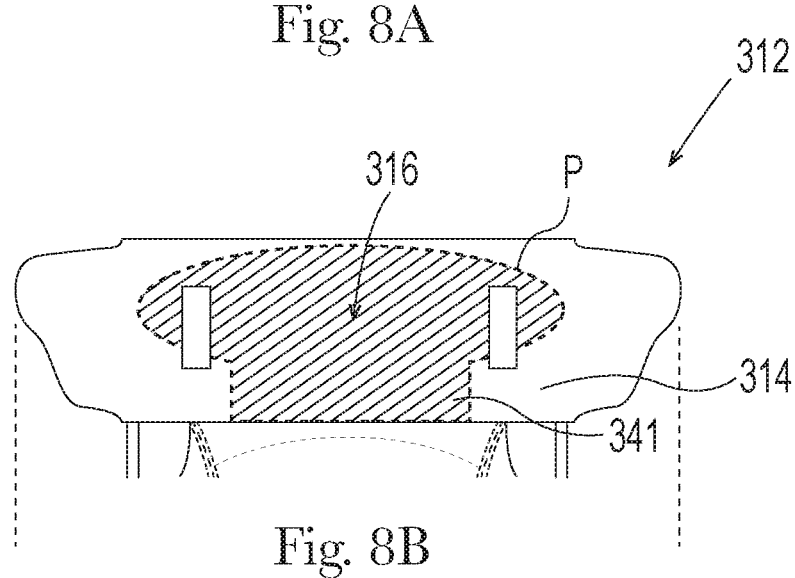

It is also contemplated that one or more secondary fastening components may be disposed outside of the anchoring zone, as illustrated in FIG. 7D. In such nonlimiting examples, a lateral inboard edge 213 of the secondary fastening component may be located a maximum lateral distance of 5 mm or less from the perimeter.

Without being bound by theory, it is believed that the decoupled zone may move independently of surrounding materials or with greater flexibility than surrounding materials, reducing the effects of the tension that arises from exudate loading. During use, a tension line forms in the article between the load, located between the wearer's thighs in the crotch region, and the secondary fastener, located proximate to the wearer's hip. In typical attachment configurations, material outboard of the tension line collapses, folds or otherwise deforms as the article narrows to fit the wearer's body. When continuously attached as shown in FIG. 3A, substantially all material surrounding the secondary fastening component folds or collapses, such that it is relocated to behind the fastening component which may result in the fastening component being placed in contact with the wearer's skin. It is believed that the decoupled zone lessens the effects of the tension line by permitting the composite or certain composite layers to operate independently in the zone. The anchoring zone 316 continues to provide the necessary bonding between the composite layers while the decoupled zone permits layers to operate more independently of the tension. While the chassis may deform about the body, the decoupling prevents materials surrounding the fastening component from being forced to move with the chassis, thereby reducing the tendency to collapse, fold or otherwise deform.

Figure 9A:
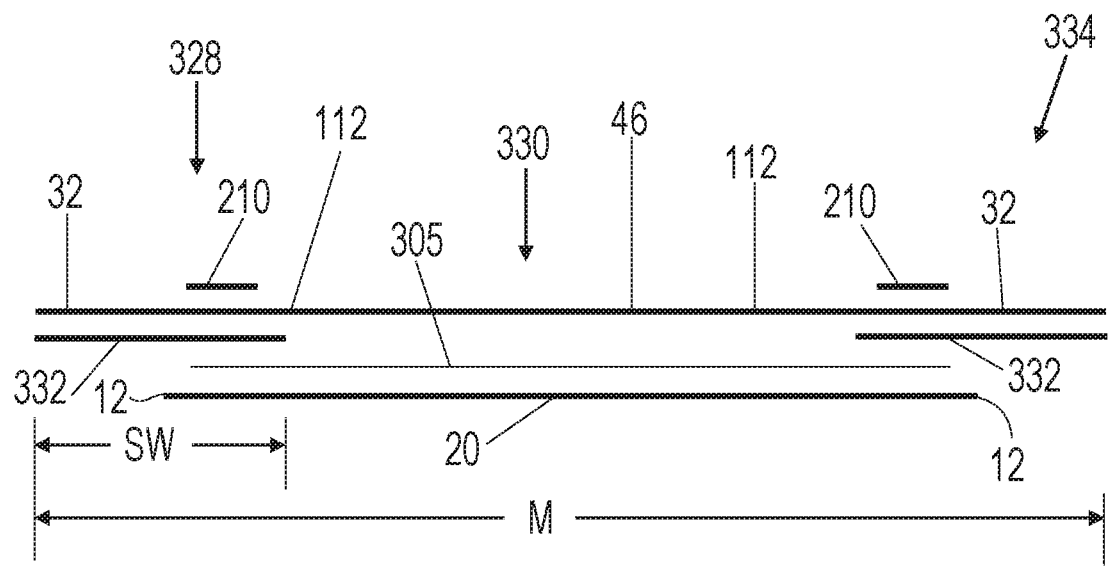
FIG. 9A is a schematic cross-sectional view of the waist region in FIG. 9 taken along line 9A-9A according a nonlimiting embodiment.
Figure 9B:
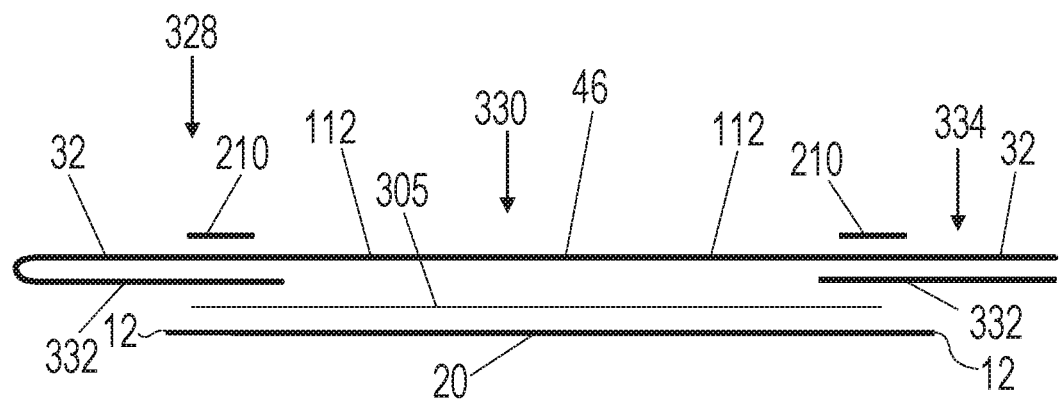
FIG. 9B is a schematic cross-sectional view of a waist region according an alternative nonlimiting embodiment.

Additionally, or alternatively, the first waist region may comprise a variation in stiffness. The stiffness of the first waist region may vary in the lateral direction. Turning to FIGS. 9-9B, in certain embodiments, the front waist region comprises a bending resistant zone 328, which is at least partially disposed outboard of the longitudinal edge 12. The bending resistant zone 328 may comprise a Stiffness of at least about 0.2 N/mm, or at least about 0.6 N/mm up to about 1 N/mm, or up to about 0.96 N/mm, or from about 0.2 N/mm to about 1.5 N/mm, or from about 0.6 N/mm to about 1 N/mm reciting for said range each 0.1 N/mm increment therein, according to the Stiffness Test Method herein. The bending resistant zone may include a portion of a combination belt structure 46. In nonlimiting examples, the bending resistant zone includes at least a portion of a front ear 32. The bending resistant zone may be formed from the layers of a lateral extension element 300. One or more stiffening components 332, such as additional nonwoven layer(s), may also be used to form the bending resistant zone.

The stiffening component may provide more stiffness to lateral extension element 300, such as an ear 32, and/or may provide or support a primary receiving component 112. Additionally, or alternatively, the stiffening component may provide or support a secondary fastening component 210. The stiffening component 332 may comprise a separate layer of material as shown in FIG. 9A and/or a folded layer of material, such as a folded belt or ear, as shown in FIG. 9B. The stiffening component may comprise a nonwoven, a film, an adhesive and combinations thereof. Additionally, or alternatively, the stiffening component may comprise intermittent bonding to create a three-dimensional structure, such structure being more bending resistant than flat structures formed from continuous bonding. In nonlimiting examples, the stiffening component is disposed in overlapping relationship with the area of attachment 305 of the lateral extension element—chassis composite 312. It is also contemplated that the stiffening component 332 be joined to the lateral extension element or to the chassis outside or separate from the composite attachment area.

The stiffening component may have dimensions that correspond to the lateral extension element. Alternatively, the stiffening component may be different in shape or area than the lateral extension element. The stiffening component may comprise a maximum width, SW, of about 30 mm to about 350 mm, or from about 45 mm to about 300 mm, or from about 50 mm to about 250 mm, reciting for each range every 10 mm increment therein. In nonlimiting examples, the stiffening component may comprise a maximum width, SW, that is less than the maximum width, M, of the lateral extension element as shown for example in FIG. 9A. In this way, less material may be utilized, and the stiffening component may be positioned only where enhanced stiffness is desired. In other nonlimiting examples, the stiffening component comprise a maximum width, SW, that is greater than or equal to the maximum width, M, of the lateral extension element. In further nonlimiting examples, the stiffening component may extend laterally outboard of a longitudinal edge 304 of the lateral extension element. In such examples, the stiffening component may serve to provide additional coverage of the wearer's skin in the hip region and/or allows for the use of different nonwovens (e.g., softer nonwovens) against the wearer's skin. As shown in FIG. 9, the stiffening component may comprise a maximum length, SL, that is substantially equal to the maximum length of the lateral extension element in the area where the stiffening component overlaps the lateral extension element, O. Alternatively, the maximum length of the stiffening component, SL, may be greater than or less than the maximum length of the belt in the area of overlap, O. In further nonlimiting examples, the stiffening component may extend laterally outboard of a lateral edge 301, 303 of the lateral extension element. In such nonlimiting examples, the stiffening component may provide additional material around a fastening component, and thereby prevent exposure of the component (e.g., hooks) to the wearer's skin.

In further nonlimiting examples, an article comprises a first bending resistant zone 328 and a second bending resistant zone 334 disposed proximate to opposite longitudinal edges 12, as shown in FIGS. 9A and 9B. The second bending resistant zone may include a portion of the lateral extension element 300, such as at least a portion of a front ear, and is at least partially disposed outboard of the longitudinal edge 12. The second bending resistant zone may comprise the same magnitude of stiffness as the first bending zone or the two zones may differ in stiffness.

Additionally, or alternatively, a bending resistant zone 328, 334 may vary in the magnitude of stiffness from a reference zone 330 by at least about 10%, or at least about 15%, or at least about 20%, or from about 10% to about 50% as determined by the Stiffness Test Method herein, reciting for said range every 5% increment therein. The reference zone 330 is disposed entirely inboard of the longitudinal edges 12. In some embodiments, the reference zone may at least partially include a portion of a combination belt structure.

In some embodiments, the rear waist region comprises variations in stiffness as described herein with respect to the front waist region.

Leg Gasketing System:

Returning to FIG. 1, the absorbent article 10 may comprise a leg gasketing system 70 attached to the chassis 20, which may comprise one or more cuffs. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 90 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximal edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134,622, Ser. No. 14/077,708; U.S. Pat. Nos. 8,939,957; 3,860,003; 7,435,243; 8,062,279.

Folded Configurations

Figure 10:
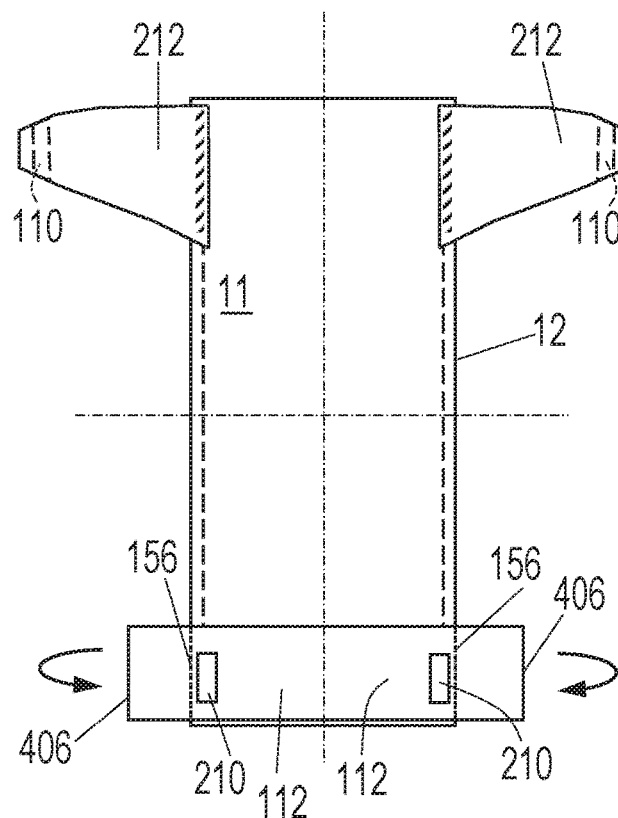
FIG. 10 is a schematic plan view of an exemplary absorbent article according to a nonlimiting embodiment. The absorbent article is shown in a flat, uncontracted state with the garment-facing surface facing the viewer.
Figure 11:
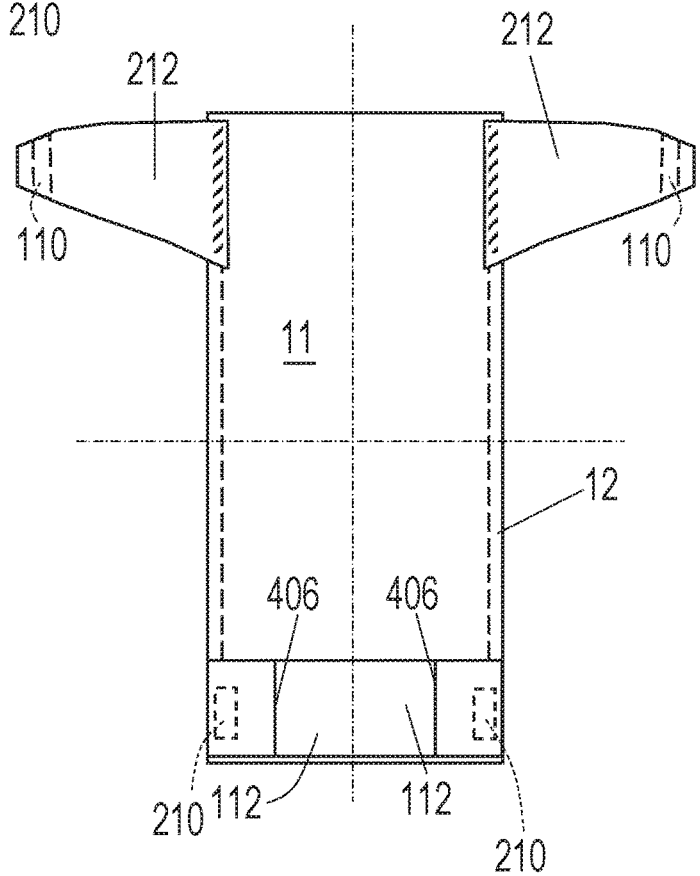
FIG. 11 is a schematic plan view of the article in FIG. 10 wherein front ears are in a folded configuration.
Figure 12:
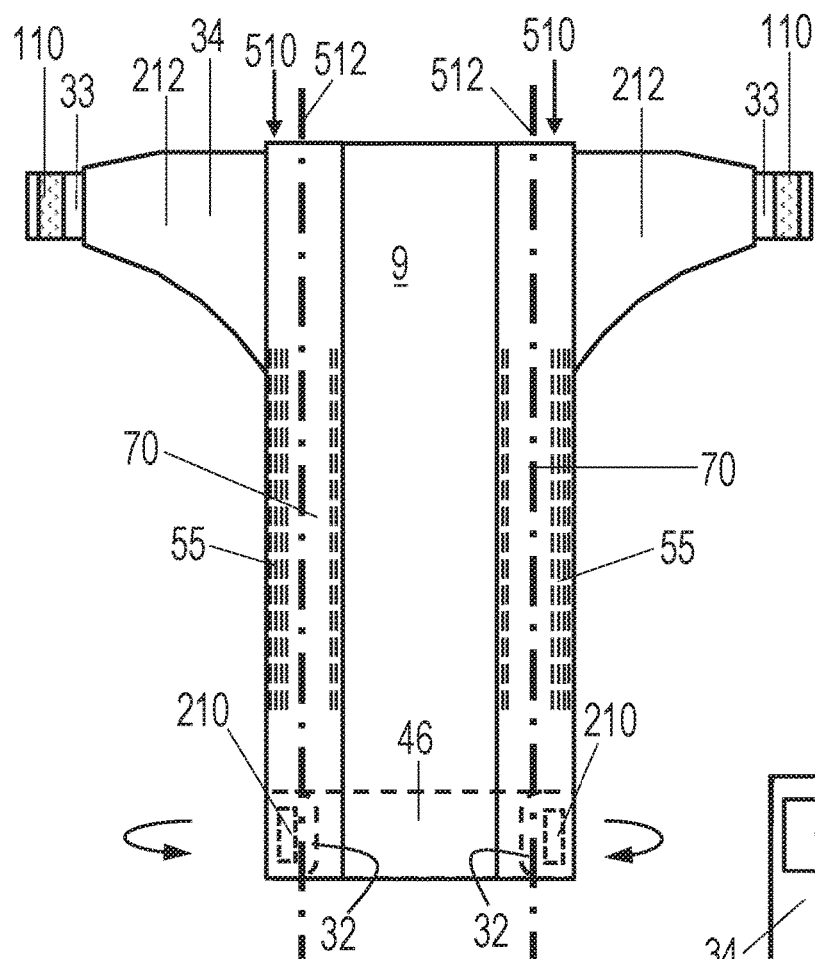
FIG. 12 is a schematic plan view of another example of an exemplary absorbent article with the wearer-facing surfaces facing the viewer, wherein the front ears are in a folded configuration.
Figure 16A:
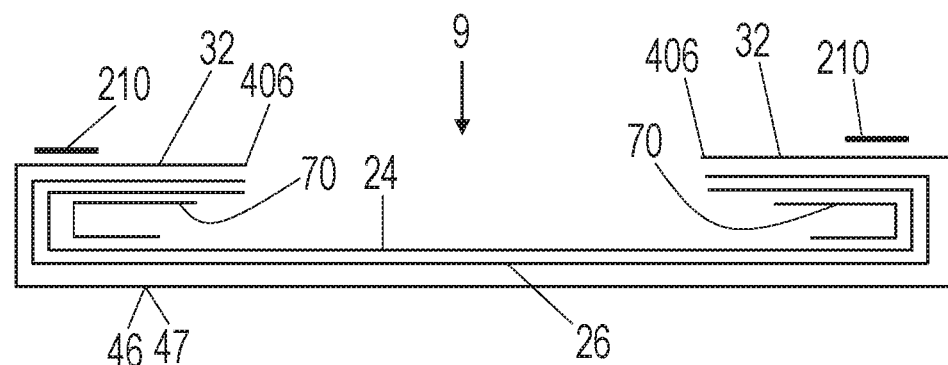
FIG. 16A is a schematic lateral cross-sectional view of another exemplary absorbent article in another nonlimiting example of folded configuration.
Figure 16B:
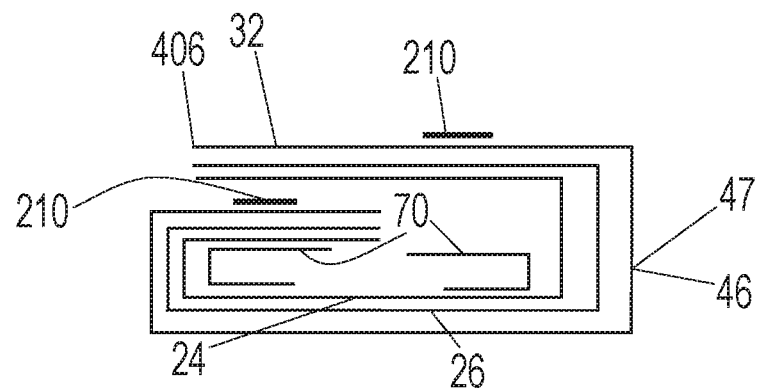
FIG. 16B is a schematic lateral cross section view of another absorbent article in another nonlimiting example of folded configuration.

Turning to FIGS. 10-16B, it may be desired to provide the absorbent article in a folded configuration, including folding the front ears. In certain embodiments, folding may serve to cover a fastening component which may be disposed on the chassis, a lateral extension element, or a combination thereof. By way of nonlimiting example, prior to or following the attachment of a combination belt structure 46 to the chassis, the front ears 32 may be folded laterally back over along longitudinal front ear fold lines 156, such that distal ends 406 of front ears 32 in such folded configuration are disposed laterally inboard of longitudinal edges 12 following attachment of the belt 46 to the chassis. As shown in FIGS. 10-11 for example, the front ear 32 may be folded toward the garment-facing surface 11 and thereby covering a secondary fastening component 210. A portion of the combination belt structure 46 may then be folded inward along another fold line 512 as is shown in FIG. 12, resulting in a z-fold configuration such as that shown in FIG. 15. In another configuration shown in FIGS. 16A and 16B, the front ear 32 may be folded toward the wearer-facing surface 9, in an e-fold configuration. In some examples having a set of opposing front ears, at least one of secondary fastening component 210 may be covered the opposite ear in the folded configuration as shown in FIG. 16B.

A folded front ear configuration may provide several advantages. First, it provides for control over the front ears 32 as the chassis moves through any further downstream processing, folding and/or packaging, reducing chances that front ears 32 will snag in any equipment, with possible resulting damage. Second, where secondary fastening components 210 of a secondary fastening system are included, folding the ears 32 over one or more secondary fastening components 210 will shield and protect the secondary fastening components from unwanted contact and interaction with other portions of the article prior to its use. For example, where secondary fastening components 210 are patches of hooks material, it may be undesirable to have them exposed when, e.g., the entire diaper is folded for packaging as will be described below, because they may undesirably snag and/or undesirably attach to other portions of the article in such folded article configuration. In order to reduce chances of a negative caregiver perception of design and/or quality, it may be desired that each fold line 156 be located no more than 10 percent of the front ear 32 width, from the proximate longitudinal edge 12.

Front ears 32 may be held in place in such folded ear configurations, for example, by releasable attachment to a secondary fastening component 210. A front ear may be held through pressure or friction. Alternatively, or in combination, each front ear 32 may be held in placed in such folded ear configuration by one or more releasable tack bonds bonding material forming a combination belt structure to itself and/or attaching material of the ear to the chassis. The releasable tack bonds may be adhesive bonds, thermal bonds or any other suitable bonding mechanism by which attachment between components is effected, but substantially non-destructive detachment thereof may be effected by gently tugging the front ear laterally outward. In one nonlimiting example, releasable tack bonds may be formed by a frangible bonding agent such as described in U.S. Pat. No. 8,454,571, disposed between the components to be attached to one another. Such a frangible bonding agent may have good adhesive strength when freshly deposited but may lose adhesive strength over time, thereby providing for good holding during manufacturing but providing for easy, non-destructive detachment at the time of consumer use. An example of a frangible bonding agent is PHO 3005 type fugitive hot-melt adhesive available from H. B. Fuller, St. Paul, Minn. In another nonlimiting example, a frangible bonding agent may be a material forming a relatively weak bond (i.e., weaker than that formed by typical diaper construction adhesives) such as but not limited to a wax, for example, paraffin wax, microcrystalline wax, synthetic wax, beeswax and other natural waxes.

Regardless of any mechanism used to hold the front ears 32 in a folded ear configuration, it may be desired that a front ear 32 may be relatively easily peeled away for unfolding from the surface from which the secondary fastening component is attached in order to facilitate unfolding without tearing or damage to the ear and/or said surface. In nonlimiting examples, the secondary fastening component may be peeled away by a peel force of about 2 N or less, or from about 0.2 N to about 2 N, or about 1 N to about 1.5 N, reciting for each range every 0.2 N therein. This peel force limit may be observed to reduce chances of caregiver difficulty and/or dissatisfaction with the diaper product, during deployment of the front ears 32 for application to a wearer. Peel force may be adjusted by techniques that will be apparent to those skilled in the art, e.g., selection and sizing of hook material to be used as secondary fastening components 210; selection of web material to be used; selection of adhesive to be used to form releasable tack bonds, size and/or pattern of releasable tack bonds, etc.

Figure 13:
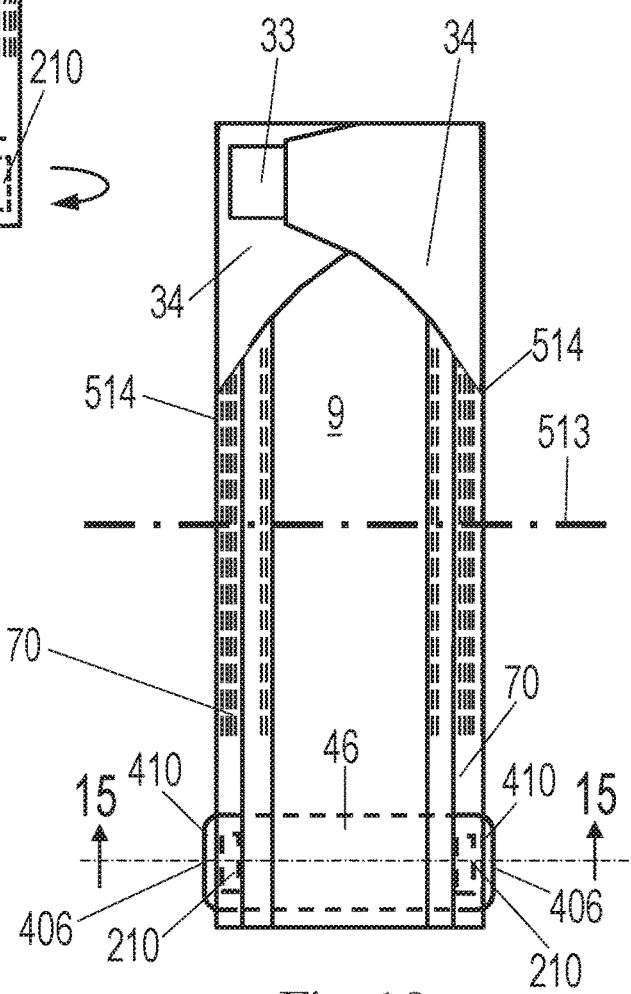
FIG. 13 is a schematic plan view of the absorbent article of FIG. 12, wearer-facing surfaces facing the viewer, shown with fastening members and side margins folded over laterally.
Figure 14:
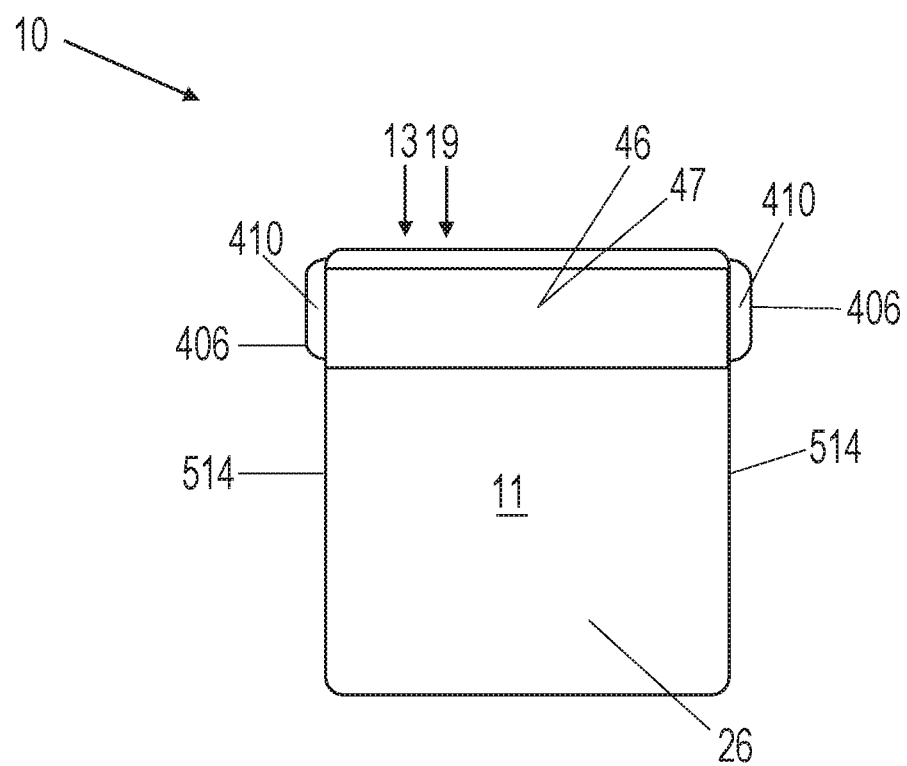
FIG. 14 is a schematic plan view of the absorbent article of FIG. 13, shown folded approximately in half about a lateral fold line with wearer-facing surfaces in and outward-facing surfaces out.
Figure 15:
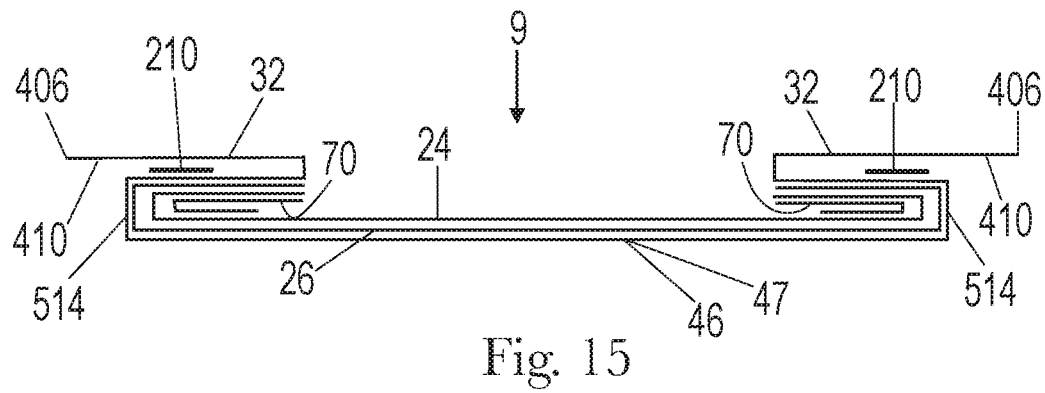
FIG. 15 is a schematic lateral cross section of the absorbent article of FIG. 13, taken through line 15-15.

It is generally desirable that absorbent articles of the type contemplated herein be folded to a more compact configuration for efficient packaging and shipping. Accordingly, in a first step, left and right side margins 510 of the article may be folded laterally inwardly, about left and right longitudinal article folding lines 512 as indicated by the curving arrows in FIG. 12, to bring the article to a first interim folded configuration depicted in FIG. 13, with left and right longitudinal folded edges 514. Referring to FIGS. 13 and 14, in a next step, the article may be folded over on itself and approximately in half lengthwise, wearer-facing surfaces in, about a lateral fold line 513, to bring it into a folded article configuration as shown in FIG. 14, which is a neat and compact configuration suitable for efficient stacking of a plurality of absorbent articles, packaging and shipment. While FIGS. 12-14 illustrate ears that are folded toward the garment-facing surface, it is to be appreciated that the folding of side margins and lateral folding can be applicable when ears are folded toward the wearer-facing side. By way of nonlimiting example, FIGS. 16A-16B illustrate a folded article where the ears 32 are folded toward the wearing-facing surface 9 along with the article side margins 510. In such examples, the ears 32 are not folded toward the garment-facing surface prior to folding the side margins.

In certain embodiments, the front ears 32, may be suitably sized, and the front ear fold lines 156 may be suitably located relative the chassis, such that the distal ends 406 of the front ears 32 are visible and easily identified and grasped by the caregiver when the diaper is in a folded diaper configuration. Referring again to FIG. 12 (depicting an example of an article with wearer-facing surfaces facing the viewer), front ears 32 are folded toward the garment-facing surface 11 and are thereby located behind the diaper in the view shown. In FIG. 13, it can be seen that tab portions 410 and distal ends 406 of front ears are not folded about the folded edges 514, but rather, are left free to protrude laterally outboard of folded edges 514. This may be appreciated also from FIG. 15. In FIGS. 13-14, it can be seen that tab portions 410 of front ears 32 extend laterally away from the folded diaper in both the interim (FIG. 13) and final (FIG. 14) folded article configurations, and as such are readily visible and available to be grasped by the caregiver upon removal from the package and partial unfolding. The section of web material 47 forming the front ears 32 may be suitably sized, and longitudinal front ear fold lines 156 (see FIG. 10) may be suitably located, relative the chassis and longitudinal article fold lines 512 (see FIG. 12), to provide such laterally extending tab portions 410.

Package

The absorbent articles 10 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 17:
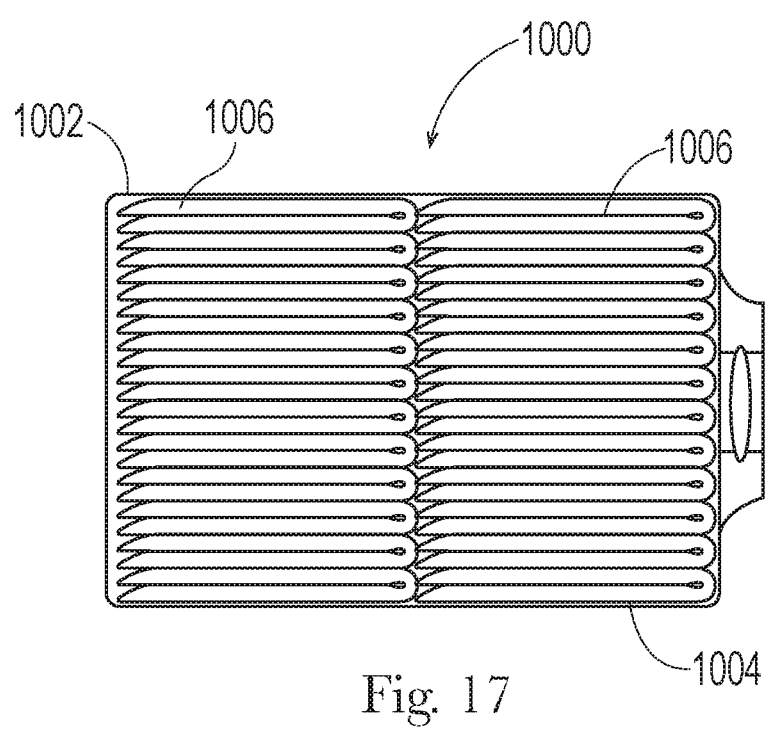
FIG. 17 is a schematic perspective view of a package in accordance with one embodiment of the present invention.

FIG. 17 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006. The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 105. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 95.

Test Methods

Hysteresis Test Method

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut with a dimension of 10 mm in the intended stretch direction of the ear X 25.4 mm in the direction perpendicular to the intended stretch direction of the ear. A specimen is collected from either an inelastic region or from an elastic region.

Test Protocol

1. Select the appropriate grips and load cell. The grips must have flat surfaces and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used.

2. Calibrate the tester according to the manufacturer's instructions.

3. Set the distance between the grips (gauge length) at 7 mm.

4. Place the specimen in the flat surfaces of the grips such that the uniform width lies along a direction perpendicular to the gauge length direction. Secure the specimen in the upper grip, let the specimen hang slack, then close the lower grip. Set the slack preload at 5 gram/force This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the 100% strain at a constant cross head speed of 70 mm/min. Report the stretched specimen length between the grips as $l_{max}$.

5(b) First cycle unloading: Hold the specimen at the 100% strain for 30 seconds and then return the crosshead to its starting position (0% strain or initial sample length, $l_{ini}$) at a constant cross head speed of 70 mm/min. Hold the specimen in the unstrained state for 1 minute.

5(c) Second cycle loading: Pull the specimen to the 100% strain at a constant cross head speed of 70 mm/min.

5(d) Second cycle unload: Next, hold the specimen at the 100% strain for 30 seconds and then return the crosshead to its starting position (i.e. 0% strain) at a constant cross head speed of 70 mm/min.

A computer data system records the force exerted on the sample during the test as a function of applied strain. From the resulting data generated, the following quantities are reported.

i. Length of specimen between the grips at a slack preload of 5 gram-force ($l_{ini}$) to the nearest 0.001 mm.

ii. Length of specimen between the grips on first cycle at the 100% strain ($l_{max}$) to the nearest 0.001 mm.

iii. Length of specimen between the grips at a second cycle load force of 7 gram-force ($l_{ext}$) to the nearest 0.001 mm.

iv. % Set, which is defined as $(l_{ext}-l_{ini})/(l_{max}-l_{ini})*100\%$ to the nearest 0.01%. The testing is repeated for six separate samples and the average and standard deviation reported.

Peel Force Test Method

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. The grips are air actuated grips designed to concentrate the entire gripping force along a single line perpendicular to the direction of testing stress having one flat surface and an opposing face from which protrudes a half round (radius=6 mm, e.g. part number: 56-163-827 from MTS Systems Corp.) or equivalent grips, to minimize slippage of the sample. The load cell is selected so that the forces measured are between 10% and 90% of the capacity of the load cell used.

The initial distance between the lines of gripping force (gauge length) is set at 30.0 mm. The load reading on the instrument is zeroed to account for the mass of the fixture and grips.

Locate the composite of interest. If the composite includes portions extending beyond the area of overlap, remove said portions along the longitudinal edge of the overlapping area. For example, if the composite comprises a belt having a front ear and the chassis, cut off the front ear along the longitudinal edge of the chassis.

Remove the composite from the remainder of the article by cutting through the article along the lateral edges of the composite, maintaining attachment between the components forming the composite. Subsequently, if the composite specimen comprises a belt joined to the garment-facing surface of the article, carefully remove the topsheet and absorbent material from the specimen. Cut the composite specimen into four comparative segments (A, B, C and D), each laterally extending 100 mm inboard from the laterally most outboard edge and having equal longitudinal dimensions. If the specimen does not allow for the lateral dimension, smaller samples can be used.

A minimum of five composite specimens are collected and cut from the same portion of identical products, and care should be taken to prevent damage of the specimen during the separation process.

Figure 18:
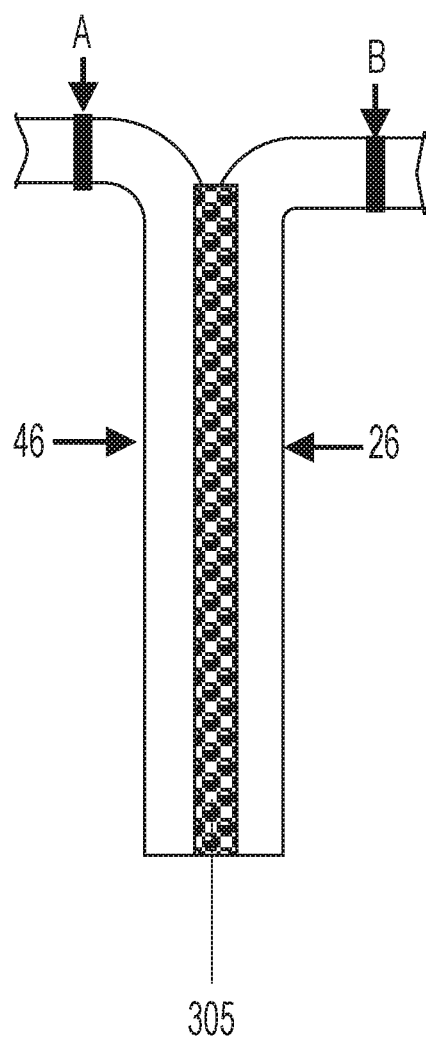
FIG. 18 is a schematic, side elevation view of a specimen for use in the Peel Test Method herein.

Referring to FIG. 18, for correct segment mounting into the test apparatus a minimum of 25 mm of unbonded material edge is required, for both substrates of the composite. If one, or both substrates, have less than 25 mm of unbonded material edge available, a section of tape such as 3M SCOTCH® 234, or similar, folded to form a flap can be adhered to the exposed material edge until the minimum 25 mm length is obtained. If no unbonded material edge is available, the composite substrates can be carefully separated using tweezers until a minimum of 5 mm unbonded edge is available.

The segment is mounted into the grips in a manner such that there is no slack and the load measured is between 0.00 N and 0.02 N. The segment is mounted in the center of the grips, such that the segment peeling direction is parallel to the applied tensile stress. The segment is placed between the grips such that the longitudinal dimension of the bonding region will be perpendicular to the grip apexes, where the first grip is holding the first substrate (e.g., belt 46) at Grip Line A and the second grip is holding the second substrate (e.g., backsheet 26) at Grip Line B, thereby peeling the first substrate from the second substrate in a 180° peeling direction. The peel test is initiated, and the segment is extended at 300 mm/min, with a data acquisition rate of at least 50 Hertz, until the substrates separate completely. The peel displacement of the segment is reported on the x axis in millimeters of crosshead travel, while the separation force of the segment is reported on the y axis in Force (gf, grams Force). The separation force (gf) is averaged from 5 mm to 30 mm of peel displacement (travel). The averaged force is normalized by the specimen bond area width, using the following formula:

$$\text{Peel Force } \frac{gf}{cm} = \left(\frac{\text{Averaged Force, grams Force}}{\text{Specimen Bond Area Width, cm}}\right).$$

This is reported as the Segment Peel Force in gf/cm. The arithmetic average of the Segment Peel Force in gf/cm and standard deviation for at least 4 of the respective segment is recorded and report as the Average Peel Force (gf/cm) for the segment.

The test is performed on each segment for each specimen. The difference between two segments is calculated as follows:

$$\Delta \text{ in Average Peel Force } \% = \\ \frac{\text{Average Peel Force for segment A} - \text{Average Peel Force for segment B}}{\text{Average Peel Force for segment A}} * 100\%$$

It is to be understood that any of the segments can be compared using the above equation and segments A and B are used as nonlimiting examples.

Stiffness Test Method

The Stiffness Test measures the bending properties of a sample.

Identify the waist region by measuring the length of the article along the longitudinal centerline from the front waist edge to the rear waist edge, and dividing said length into three equal sections. For samples in the front waist region, remove the specimens from the front third of the article. For samples in the rear waist region, remove the specimens from the last third of the article.

Cut a rectangular section of material measuring at least 30 mm by 50 mm, excluding any primary fastening components or secondary fastening components. Cut the specimen such that the 50 mm dimension in the longitudinal direction of the article and parallel to the longitudinal axis. Maintain the longitudinal direction relative to the product and note the garment facing side of the specimen. If the specimen does not allow these dimensions, smaller samples can be used.

Specimens are conditioned at 23° C.±3° C. and 50%±2% relative humidity two hours prior to testing.

The bending properties of a sample are measured on a constant rate of extension tensile tester (a suitable instrument is the MTS Alliance using Testworks 4.0 Software, as available from MTS Systems Corp., Eden Prairie, Minn.) using a load cell for which the forces measured are within 10% to 90% of the limit of the cell. All testing is performed in a room controlled at 23° C.±3° C. and 50%±2% relative humidity.

The bottom stationary fixture of the tensile tester consists of two bars 3.175 mm in diameter by 60 mm in length, made of polished stainless steel each mounted on its own fork in linear ball bearing to reduce COF affect. These two bars are mounted horizontally, aligned front to back and parallel to each other, with top radii of the bars vertically aligned. Furthermore, the fixture allows for the two bars to be move horizontally away from each other on a track so that a gap can be set between them while maintaining their orientation. The top movable fixture consists of a third bar also 3.175 mm in diameter by 60 mm in length, made of polished stainless steel mounted on a fork in linear ball bearing to reduce COF affect. When in place the bar of the top fixture is parallel to, and aligned front to back with the bars of the bottom fixture. Both fixtures include an integral adapter appropriate to fit the respective position on the tensile tester frame and lock into position such that the bars are orthogonal to the motion of the crossbeam of the tensile tester.

Set the gap between the bars of the lower fixture to 5 mm±0.1 mm (center of bar to center of bar) with the upper bar centered at the midpoint between the lower bars. Set the gage (bottom of top bar to top of blower bars) to 3 mm.

Measure the caliper of each specimen, using a digital caliper (e.g. Ono Sokki GS-503 or equivalent) fitted with a 25 mm diameter foot that applies a confining pressure of 0.1 PSI. Read the caliper (mm) 5 sec after resting the foot on the sample and record to the nearest 0.01 mm.

Program the tensile tester for a compression test, to move the crosshead down at a rate of 0.5 mm/sec until the upper bar touches the top surface of the specimen, then continue for an additional 8 mm collecting force (N) and displacement mm data at 200 Hz, and return the crosshead to its original gage. Orient specimens with garment facing side toward the upper bar. Load the specimen such that it spans the two lower bars with its lateral centerline centered under the upper bar and its longitudinal centerline aligned to the center point of the upper bar's length. Zero the crosshead and load cell. Start the run and collect data.

Construct a graph of force (N) verses displacement (mm). Read the Maximum Peak Force (N) from the graph and record to the nearest 0.1N. Report the slope as N/mm to the nearest 0.1 N/mm.

Measures are repeated in like fashion for 3 specimens from the same location. The arithmetic average slope of the three specimens is reported as the sample's Stiffness to the nearest 0.1 N/mm.

A difference in magnitude between two samples can be determined using the following equation:

$$\Delta \text{Magnitude} = \frac{\text{Stiffness for Sample } A - \text{Stiffness for Sample } B}{\text{Stiffness for Sample } A}$$

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 17). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a first waist region, a second waist region, a crotch region disposed between the first and second waist regions;
a chassis comprising a topsheet, a backsheet, and an absorbent core disposed between the topsheet and the backsheet;
a primary fastening system and a secondary fastening system, wherein the primary fastening system comprises a primary fastening component disposed in the second waist region and a primary receiving component disposed in the first waist region and operatively engageable with the primary fastening component; and wherein the secondary fastening system comprises a secondary fastening component disposed in the first waist region and a secondary receiving component disposed in the second waist region and operatively engageable with the secondary fastening component;
a composite comprising one or more layers of a lateral extension element and the chassis;
an anchoring zone wherein the one or more layers of the composite are joined, the anchoring zone being defined by a perimeter; and
a decoupled zone adjacent to the anchoring zone and disposed outside of the perimeter,
wherein at least a portion of the secondary fastening component is disposed in the anchoring zone and wherein a portion of the composite is longitudinally inboard of the secondary fastening component and within the decoupled zone, and
wherein a portion of the composite is disposed laterally outboard of the secondary fastening component and is within the decoupled zone.

2. The absorbent article of claim 1 wherein the decoupled zone comprises a zone of detachment.

3. The absorbent article of claim 1 wherein the decoupled zone comprises a zone of weakness.

4. The absorbent article of claim 1 wherein the lateral extension element comprises one or more layers of a combination belt structure.

5. The absorbent article of claim 1 wherein at least about 25% of the secondary fastening component is disposed within the anchoring zone.

6. The absorbent article of claim 1 wherein a portion of the composite is disposed laterally inboard of the secondary fastening component and is within the decoupled zone.

7. The absorbent article of claim 1 wherein the perimeter comprises at least one straight line portion.

8. The absorbent article of claim 1 wherein the perimeter comprises at least one curved portion.

9. The absorbent article of claim 1 wherein the perimeter comprises a plurality of discrete bond sites.

10. The absorbent article of claim 1 further comprising an elastic waistband.

11. An absorbent article comprising:
a first waist region, a second waist region, a crotch region disposed between the first and second waist regions;
a chassis comprising a topsheet, a backsheet, and an absorbent core disposed between the topsheet and backsheet;
a primary fastening system and a secondary fastening system, wherein the primary fastening system comprises a primary fastening component disposed in the second waist region and a primary receiving component disposed in the first waist region and operatively engageable with the primary fastening component; and
a composite comprising one or more layers of the chassis, wherein the one or more layers of the composite are joined in an anchoring zone and a decoupled zone adjacent to the anchoring zone,
wherein the secondary fastening system comprises a secondary fastening component at least partially disposed in a bending resistant zone of the first waist region and a secondary receiving component disposed in the second waist region and operatively engageable with the secondary fastening component;
wherein the bending resistant zone comprises a stiffening component;
wherein the stiffening component is in at least partial overlapping relationship with the secondary fastening component;
wherein the bending resistant zone comprises a stiffness of at least 0.2 N/mm; and
wherein a portion of the composite is disposed laterally outboard of the secondary fastening component and is within the decoupled zone.

12. The absorbent article of claim 11 further comprising a lateral extension element, wherein the lateral extension element is in at least partial overlapping relationship with the bending resistant zone and wherein the lateral extension element comprises a first lateral edge and a second lateral edge, wherein the secondary fastening component is disposed between the first and second lateral edges.

13. The absorbent article of claim 11, wherein the stiffening component is selected from the group consisting of folded material, a nonwoven, a film, adhesive and combinations thereof.

14. The absorbent article of claim 11 further comprising an elastic waistband.

15. An absorbent article comprising:
a first waist region, a second waist region, a crotch region disposed between the first and second waist regions;
a chassis comprising a topsheet, a backsheet, and an absorbent core disposed between the topsheet and backsheet; and
a primary fastening system and a secondary fastening system, wherein the primary fastening system comprises a primary fastening component disposed in the second waist region and a primary receiving component disposed in the first waist region and operatively engageable with the primary fastening component; and
wherein the secondary fastening system comprises a secondary fastening component disposed in the first waist region and a secondary receiving component disposed in the second waist region and operatively engageable with the secondary fastening component;
a composite comprising an anchoring zone and a decoupled zone;
a lateral extension element joined to the chassis in the first waist region in the anchoring zone defined by a perimeter;
wherein the anchoring zone comprises a varied width, as measured in a lateral direction, having a maximum width, $W_{AZmax}$, and a minimum width, $W_{AZmin}$, wherein the maximum width, $W_{AZmax}$, is in an area that is longitudinally outboard of the minimum width, and
wherein a portion of the composite is disposed laterally outboard of the secondary fastening component and is within the decoupled zone.

16. The absorbent article of claim 15 wherein the perimeter comprises a curvilinear portion.

17. The absorbent article of claim 15 wherein the perimeter comprises a straight portion.

18. The absorbent article of claim 15 wherein the first waist region comprises a bending resistant zone having a Stiffness of at least 0.2 N/mm.

* * * * *